US007588825B2

(12) United States Patent
Bell et al.

(10) Patent No.: US 7,588,825 B2
(45) Date of Patent: Sep. 15, 2009

(54) EMBOLIC COMPOSITIONS

(75) Inventors: Barbara Bell, Sudbury, MA (US); Thomas V. Casey, II, Grafton, MA (US); William J. Shaw, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 997 days.

(21) Appl. No.: 10/700,970

(22) Filed: Nov. 4, 2003

(65) Prior Publication Data

US 2004/0091543 A1 May 13, 2004

Related U.S. Application Data

(63) Continuation-in-part of application No. 10/278,248, filed on Oct. 23, 2002.

(51) Int. Cl.
*B32B 5/66* (2006.01)
(52) U.S. Cl. .................. 428/402; 428/403; 428/404; 428/405; 428/406; 428/407; 623/23.73
(58) Field of Classification Search .......... 428/402–407
See application file for complete search history.

(56) References Cited

U.S. PATENT DOCUMENTS

| | | | |
|---|---|---|---|
| 2,275,154 A | 3/1942 | Merrill et al. |
| 2,609,347 A | 9/1952 | Wilson |
| 3,663,470 A | 5/1972 | Nishimura et al. |
| 3,737,398 A | 6/1973 | Yamaguchi |
| 3,957,933 A | 5/1976 | Egli et al. |
| 4,025,686 A | 5/1977 | Zion |
| 4,034,759 A | 7/1977 | Haerr |
| 4,055,377 A | 10/1977 | Erickson et al. |
| 4,076,640 A | 2/1978 | Forgensi et al. |
| 4,094,848 A | 6/1978 | Naito |
| 4,096,230 A | 6/1978 | Haerr |
| 4,098,728 A | 7/1978 | Rosenblatt |
| 4,110,529 A | 8/1978 | Stoy |
| 4,159,719 A | 7/1979 | Haerr |
| 4,191,672 A | 3/1980 | Salome et al. |
| 4,198,318 A | 4/1980 | Stowell et al. |
| 4,243,794 A | 1/1981 | White et al. |
| 4,246,208 A | 1/1981 | Dundas |
| 4,266,030 A | 5/1981 | Tschang et al. |
| 4,268,495 A | 5/1981 | Muxfeldt et al. |
| 4,271,281 A | 6/1981 | Kelley et al. |
| 4,402,319 A | 9/1983 | Handa et al. |
| 4,413,070 A | 11/1983 | Rembaum |
| 4,427,794 A | 1/1984 | Lange et al. |
| 4,428,869 A | 1/1984 | Munteanu et al. |
| 4,429,062 A | 1/1984 | Pasztor et al. |
| 4,442,843 A | 4/1984 | Rasor et al. |
| 4,444,961 A | 4/1984 | Timm |
| 4,452,773 A | 6/1984 | Molday |
| 4,456,693 A | 6/1984 | Welsh |
| 4,459,145 A | 7/1984 | Elsholz |
| 4,472,552 A | 9/1984 | Blouin |
| 4,477,255 A | 10/1984 | Pasztor et al. |
| 4,492,720 A | 1/1985 | Mosier |
| 4,515,906 A | 5/1985 | Friesen et al. |
| 4,522,953 A | 6/1985 | Barby et al. |
| 4,542,178 A | 9/1985 | Zimmermann et al. |
| 4,551,132 A | 11/1985 | Pasztor et al. |
| 4,551,436 A | 11/1985 | Johnson et al. |
| 4,573,967 A | 3/1986 | Hargrove et al. |
| 4,622,362 A | 11/1986 | Rembaum |
| 4,623,706 A | 11/1986 | Timm et al. |
| 4,629,464 A | 12/1986 | Takata et al. |
| 4,640,807 A | 2/1987 | Afghan et al. |
| 4,657,756 A | 4/1987 | Rasor et al. |
| 4,661,137 A | 4/1987 | Garnier et al. |
| 4,663,358 A | 5/1987 | Hyon et al. |
| 4,671,954 A | 6/1987 | Goldberg et al. |
| 4,674,480 A | 6/1987 | Lemelson |
| 4,675,113 A | 6/1987 | Graves et al. |
| 4,678,710 A | 7/1987 | Sakimoto et al. |
| 4,678,814 A | 7/1987 | Rembaum |
| 4,680,320 A | 7/1987 | Uku et al. |
| 4,681,119 A | 7/1987 | Rasor et al. |
| 4,695,466 A | 9/1987 | Morishita et al. |
| 4,713,076 A | 12/1987 | Draenert |
| 4,742,086 A | 5/1988 | Masamizu et al. |

(Continued)

FOREIGN PATENT DOCUMENTS

AU          A-76186/98          10/1998

(Continued)

OTHER PUBLICATIONS

Kim et al., "Hollow Silica Spheres of Controlled Size and Porosity by Sol-Gel Processing," *J. Am. Ceram. Soc.*, 74(8):1987-1992 (Aug. 1991).

(Continued)

*Primary Examiner*—Leszek Kiliman
(74) *Attorney, Agent, or Firm*—Fish & Richardson P.C.

(57) ABSTRACT

Embolic compositions and methods of delivering the compositions are disclosed. In some embodiments, an embolic composition includes a first collection of particles having a first shape, and a second collection of particles having a second shape different than the first shape.

21 Claims, 11 Drawing Sheets

U.S. PATENT DOCUMENTS

| | | |
|---|---|---|
| 4,743,507 A | 5/1988 | Franses et al. |
| 4,772,635 A | 9/1988 | Mitschker et al. |
| 4,782,097 A | 11/1988 | Jain et al. |
| 4,789,501 A | 12/1988 | Day et al. |
| 4,793,980 A | 12/1988 | Torobin |
| 4,795,741 A | 1/1989 | Leshchiner et al. |
| 4,801,458 A | 1/1989 | Hidaka et al. |
| 4,804,366 A | 2/1989 | Zdeb et al. |
| 4,819,637 A | 4/1989 | Dormandy, Jr. et al. |
| 4,822,535 A | 4/1989 | Ekman et al. |
| 4,833,237 A | 5/1989 | Kawamura et al. |
| 4,850,978 A | 7/1989 | Dudar et al. |
| 4,859,711 A | 8/1989 | Jain et al. |
| 4,863,972 A | 9/1989 | Itagaki et al. |
| 4,897,255 A | 1/1990 | Fritzberg et al. |
| 4,929,400 A | 5/1990 | Rembaum et al. |
| 4,933,372 A | 6/1990 | Feibush et al. |
| 4,946,899 A | 8/1990 | Kennedy et al. |
| 4,954,399 A | 9/1990 | Tani et al. |
| 4,981,625 A | 1/1991 | Rhim et al. |
| 4,990,340 A | 2/1991 | Hidaka et al. |
| 4,999,188 A | 3/1991 | Sloldovnik et al. |
| 5,007,940 A | 4/1991 | Berg |
| 5,011,677 A | 4/1991 | Day et al. |
| H915 H | 5/1991 | Gibbs |
| 5,015,423 A | 5/1991 | Eguchi et al. |
| 5,032,117 A | 7/1991 | Motta |
| 5,034,324 A | 7/1991 | Shinozaki et al. |
| 5,047,438 A | 9/1991 | Feibush et al. |
| 5,079,274 A | 1/1992 | Schneider et al. |
| 5,091,205 A | 2/1992 | Fan |
| 5,106,903 A | 4/1992 | Vanderhoff et al. |
| 5,114,421 A | 5/1992 | Polak |
| 5,116,387 A | 5/1992 | Berg |
| 5,120,349 A | 6/1992 | Stewart et al. |
| 5,125,892 A | 6/1992 | Drudik |
| 5,147,631 A | 9/1992 | Glajch et al. |
| 5,147,937 A | 9/1992 | Frazza et al. |
| 5,149,543 A | 9/1992 | Cohen et al. |
| 5,158,573 A | 10/1992 | Berg |
| 5,171,214 A | 12/1992 | Kolber et al. |
| 5,171,217 A | 12/1992 | March et al. |
| 5,181,921 A | 1/1993 | Makita et al. |
| 5,190,760 A | 3/1993 | Baker |
| 5,190,766 A | 3/1993 | Ishihara |
| 5,192,301 A * | 3/1993 | Kamiya et al. ............... 606/213 |
| 5,202,352 A | 4/1993 | Okada et al. |
| 5,216,096 A | 6/1993 | Hattori et al. |
| 5,253,991 A | 10/1993 | Yokota et al. |
| 5,260,002 A | 11/1993 | Wang |
| 5,262,176 A | 11/1993 | Palmacci et al. |
| 5,263,992 A | 11/1993 | Guire |
| 5,288,763 A | 2/1994 | Li et al. |
| 5,292,814 A | 3/1994 | Bayer et al. |
| 5,302,369 A | 4/1994 | Day et al. |
| 5,314,974 A | 5/1994 | Ito et al. |
| 5,316,774 A | 5/1994 | Eury et al. |
| RE34,640 E | 6/1994 | Kennedy et al. |
| 5,320,639 A | 6/1994 | Rudnick |
| 5,328,936 A | 7/1994 | Leifholtz et al. |
| 5,336,263 A | 8/1994 | Ersek et al. |
| 5,344,452 A | 9/1994 | Lemperle |
| 5,344,867 A | 9/1994 | Morgan et al. |
| 5,354,290 A | 10/1994 | Gross |
| 5,369,133 A | 11/1994 | Ihm et al. |
| 5,369,163 A | 11/1994 | Chiou et al. |
| 5,382,260 A | 1/1995 | Dormandy, Jr. et al. |
| 5,384,124 A | 1/1995 | Courteille et al. |
| 5,397,303 A | 3/1995 | Sancoff et al. |
| 5,398,851 A | 3/1995 | Sancoff et al. |
| 5,403,870 A | 4/1995 | Gross |
| 5,409,125 A | 4/1995 | Kimber et al. |
| 5,417,982 A | 5/1995 | Modi |
| 5,431,174 A | 7/1995 | Knute |
| 5,435,645 A | 7/1995 | Faccioli et al. |
| 5,443,495 A | 8/1995 | Buscemi et al. |
| 5,456,693 A | 10/1995 | Conston et al. |
| 5,468,801 A | 11/1995 | Antonelli et al. |
| 5,469,854 A | 11/1995 | Unger et al. |
| 5,476,472 A | 12/1995 | Dormandy, Jr. et al. |
| 5,484,584 A | 1/1996 | Wallace et al. |
| 5,490,984 A | 2/1996 | Freed |
| 5,494,682 A | 2/1996 | Cohen et al. |
| 5,494,940 A | 2/1996 | Unger et al. |
| 5,512,604 A | 4/1996 | Demopolis |
| 5,514,090 A | 5/1996 | Kriesel et al. |
| 5,525,334 A | 6/1996 | Ito et al. |
| 5,534,589 A | 7/1996 | Hager et al. |
| 5,541,031 A | 7/1996 | Yamashita et al. |
| 5,542,935 A | 8/1996 | Unger et al. |
| 5,553,741 A | 9/1996 | Sancoff et al. |
| 5,556,391 A | 9/1996 | Cercone et al. |
| 5,556,610 A | 9/1996 | Yan et al. |
| 5,558,255 A | 9/1996 | Sancoff et al. |
| 5,558,822 A | 9/1996 | Gitman et al. |
| 5,558,856 A | 9/1996 | Klaveness et al. |
| 5,559,266 A | 9/1996 | Klaveness et al. |
| 5,567,415 A | 10/1996 | Porter |
| 5,569,193 A | 10/1996 | Hofstetter et al. |
| 5,569,449 A | 10/1996 | Klaveness et al. |
| 5,569,468 A | 10/1996 | Modi |
| 5,571,182 A | 11/1996 | Ersek et al. |
| 5,580,575 A | 12/1996 | Unger et al. |
| 5,583,162 A | 12/1996 | Li et al. |
| 5,585,112 A | 12/1996 | Unger et al. |
| 5,595,821 A | 1/1997 | Hager et al. |
| 5,622,657 A | 4/1997 | Takada et al. |
| 5,624,685 A | 4/1997 | Takahashi et al. |
| 5,635,215 A | 6/1997 | Boschetti et al. |
| 5,637,087 A | 6/1997 | O'Neil et al. |
| 5,639,710 A | 6/1997 | Lo et al. |
| 5,648,095 A | 7/1997 | Illum et al. |
| 5,648,100 A | 7/1997 | Boschetti et al. |
| 5,650,116 A | 7/1997 | Thompson |
| 5,651,990 A | 7/1997 | Takada et al. |
| 5,653,922 A | 8/1997 | Li et al. |
| 5,657,756 A | 8/1997 | Vrba |
| 5,681,576 A | 10/1997 | Henry |
| 5,695,480 A | 12/1997 | Evans et al. |
| 5,695,740 A | 12/1997 | Porter |
| 5,698,271 A | 12/1997 | Liberti et al. |
| 5,701,899 A | 12/1997 | Porter |
| 5,715,824 A | 2/1998 | Unger et al. |
| 5,716,981 A | 2/1998 | Hunter et al. |
| 5,718,884 A | 2/1998 | Klaveness et al. |
| 5,723,269 A | 3/1998 | Akagi et al. |
| 5,725,534 A | 3/1998 | Rasmussen |
| 5,733,925 A | 3/1998 | Kunz et al. |
| 5,741,331 A | 4/1998 | Pinchuk |
| 5,746,734 A | 5/1998 | Dormandy, Jr. et al. |
| 5,752,974 A | 5/1998 | Rhee et al. |
| 5,756,127 A | 5/1998 | Grisoni et al. |
| 5,760,097 A | 6/1998 | Li et al. |
| 5,766,147 A | 6/1998 | Sancoff et al. |
| 5,770,222 A | 6/1998 | Unger et al. |
| 5,779,668 A | 7/1998 | Grabenkort |
| 5,785,642 A | 7/1998 | Wallace et al. |
| 5,785,682 A | 7/1998 | Grabenkort |
| 5,792,478 A | 8/1998 | Lawin et al. |
| 5,795,562 A | 8/1998 | Klaveness et al. |
| 5,797,953 A | 8/1998 | Tekulve |
| 5,807,323 A | 9/1998 | Kriesel et al. |
| 5,813,411 A | 9/1998 | Van Bladel et al. |
| 5,823,198 A | 10/1998 | Jones et al. |

| Patent | Date | Inventor |
|---|---|---|
| 5,827,502 A | 10/1998 | Klaveness et al. |
| 5,827,531 A | 10/1998 | Morrison et al. |
| 5,830,178 A | 11/1998 | Jones et al. |
| 5,833,361 A | 11/1998 | Funk |
| 5,840,387 A | 11/1998 | Berlowitz-Tarrant et al. |
| 5,846,518 A | 12/1998 | Yan et al. |
| 5,853,752 A | 12/1998 | Unger et al. |
| 5,855,615 A | 1/1999 | Bley et al. |
| 5,863,957 A | 1/1999 | Li et al. |
| 5,876,372 A | 3/1999 | Grabenkort et al. |
| 5,877,224 A | 3/1999 | Brocchini et al. |
| 5,885,216 A | 3/1999 | Evans, III et al. |
| 5,885,547 A | 3/1999 | Gray |
| 5,888,546 A | 3/1999 | Ji et al. |
| 5,888,930 A | 3/1999 | Smith et al. |
| 5,891,155 A | 4/1999 | Irie |
| 5,894,022 A | 4/1999 | Ji et al. |
| 5,895,398 A | 4/1999 | Wensel et al. |
| 5,895,411 A | 4/1999 | Irie |
| 5,899,877 A | 5/1999 | Leibitzki et al. |
| 5,902,832 A | 5/1999 | Van Bladel et al. |
| 5,902,834 A | 5/1999 | Porrvik |
| 5,922,025 A | 7/1999 | Hubbard |
| 5,922,304 A | 7/1999 | Unger |
| 5,928,626 A | 7/1999 | Klaveness et al. |
| 5,935,553 A | 8/1999 | Unger et al. |
| 5,951,160 A | 9/1999 | Ronk |
| 5,957,848 A | 9/1999 | Sutton et al. |
| 5,959,073 A | 9/1999 | Schlameus et al. |
| 6,003,566 A | 12/1999 | Thibault et al. |
| 6,015,546 A | 1/2000 | Sutton et al. |
| 6,027,472 A | 2/2000 | Kriesel et al. |
| 6,028,066 A | 2/2000 | Unger |
| 6,047,861 A | 4/2000 | Vidal et al. |
| 6,048,908 A | 4/2000 | Kitagawa |
| 6,051,247 A | 4/2000 | Hench et al. |
| 6,056,721 A | 5/2000 | Shulze |
| 6,056,844 A | 5/2000 | Guiles et al. |
| 6,059,766 A | 5/2000 | Greff |
| 6,063,068 A | 5/2000 | Fowles et al. |
| 6,071,495 A | 6/2000 | Unger et al. |
| 6,071,497 A | 6/2000 | Steiner et al. |
| 6,073,759 A | 6/2000 | Lamborne et al. |
| 6,090,925 A | 7/2000 | Woiszwillo et al. |
| 6,096,344 A | 8/2000 | Liu et al. |
| 6,099,864 A | 8/2000 | Morrison et al. |
| 6,100,306 A | 8/2000 | Li et al. |
| 6,139,963 A | 10/2000 | Fujii et al. |
| 6,149,623 A | 11/2000 | Reynolds |
| 6,160,084 A | 12/2000 | Langer et al. |
| 6,162,377 A | 12/2000 | Ghosh et al. |
| 6,165,193 A | 12/2000 | Greene, Jr. et al. |
| 6,179,817 B1 | 1/2001 | Zhong |
| 6,191,193 B1 | 2/2001 | Lee et al. |
| 6,214,331 B1 | 4/2001 | Vanderhoff et al. |
| 6,214,384 B1 | 4/2001 | Pallado et al. |
| 6,224,630 B1 | 5/2001 | Bao et al. |
| 6,224,794 B1 | 5/2001 | Amsden et al. |
| 6,235,224 B1 | 5/2001 | Mathiowitz et al. |
| 6,238,403 B1 | 5/2001 | Greene, Jr. et al. |
| 6,245,090 B1 | 6/2001 | Gilson et al. |
| 6,251,661 B1 | 6/2001 | Urabe et al. |
| 6,258,338 B1 | 7/2001 | Gray |
| 6,261,585 B1 | 7/2001 | Sefton et al. |
| 6,264,861 B1 | 7/2001 | Tavernier et al. |
| 6,267,154 B1 | 7/2001 | Felicelli et al. |
| 6,268,053 B1 | 7/2001 | Woiszwillo et al. |
| 6,277,392 B1 | 8/2001 | Klein |
| 6,280,457 B1 | 8/2001 | Wallace et al. |
| 6,291,605 B1 | 9/2001 | Freeman et al. |
| 6,296,604 B1 | 10/2001 | Garibaldi et al. |
| 6,296,622 B1 | 10/2001 | Kurz et al. |
| 6,296,632 B1 | 10/2001 | Luscher et al. |
| 6,306,418 B1 | 10/2001 | Bley |
| 6,306,419 B1 | 10/2001 | Vachon et al. |
| 6,306,425 B1 | 10/2001 | Tice et al. |
| 6,306,427 B1 | 10/2001 | Annonier et al. |
| 6,312,407 B1 | 11/2001 | Zadno-Azizi et al. |
| 6,312,942 B1 | 11/2001 | Plüss-Wenzinger et al. |
| 6,315,709 B1 | 11/2001 | Garibaldi et al. |
| 6,335,384 B1 | 1/2002 | Evans et al. |
| 6,344,182 B1 | 2/2002 | Sutton et al. |
| 6,355,275 B1 | 3/2002 | Klein |
| 6,368,658 B1 | 4/2002 | Schwarz et al. |
| 6,379,373 B1 | 4/2002 | Sawhney et al. |
| 6,388,043 B1 | 5/2002 | Langer et al. |
| 6,394,965 B1 | 5/2002 | Klein |
| 6,423,332 B1 | 7/2002 | Huxel et al. |
| 6,432,437 B1 | 8/2002 | Hubbard |
| 6,436,112 B2 | 8/2002 | Wensel et al. |
| 6,443,941 B1 | 9/2002 | Slepian et al. |
| 6,458,296 B1 | 10/2002 | Heinzen et al. |
| 6,476,069 B2 | 11/2002 | Krall et al. |
| 6,495,155 B1 | 12/2002 | Tice et al. |
| 6,544,503 B1 | 4/2003 | Vanderhoff et al. |
| 6,544,544 B2 | 4/2003 | Hunter et al. |
| 6,545,097 B2 | 4/2003 | Pinchuk et al. |
| 6,575,896 B2 | 6/2003 | Silverman et al. |
| 6,602,261 B2 | 8/2003 | Greene, Jr. et al. |
| 6,602,524 B2 | 8/2003 | Batich et al. |
| 6,605,111 B2 | 8/2003 | Bose et al. |
| 6,629,947 B1 | 10/2003 | Sahatjian et al. |
| 6,632,531 B2 | 10/2003 | Blankenship |
| 6,652,883 B2 | 11/2003 | Goupil et al. |
| 6,673,050 B1 | 1/2004 | Farris |
| 6,680,046 B1 | 1/2004 | Boschetti |
| 6,699,222 B1 | 3/2004 | Jones et al. |
| 6,723,067 B2 | 4/2004 | Nielson |
| 7,131,997 B2 * | 11/2006 | Bourne et al. ............ 623/23.72 |
| 2001/0001835 A1 | 5/2001 | Greene, Jr. et al. |
| 2001/0016210 A1 | 8/2001 | Mathiowitz et al. |
| 2001/0036451 A1 | 11/2001 | Goupil et al. |
| 2001/0051670 A1 | 12/2001 | Goupil et al. |
| 2002/0054912 A1 | 5/2002 | Kim et al. |
| 2002/0061954 A1 | 5/2002 | Davis et al. |
| 2002/0160109 A1 | 10/2002 | Yeo et al. |
| 2002/0182190 A1 | 12/2002 | Naimark et al. |
| 2002/0197208 A1 | 12/2002 | Ruys et al. |
| 2003/0007928 A1 | 1/2003 | Gray |
| 2003/0032935 A1 | 2/2003 | Damiano et al. |
| 2003/0108614 A1 | 6/2003 | Volkonsky et al. |
| 2003/0183962 A1 | 10/2003 | Buiser et al. |
| 2003/0185895 A1 | 10/2003 | Lanphere et al. |
| 2003/0185896 A1 | 10/2003 | Buiser et al. |
| 2003/0187320 A1 | 10/2003 | Freyman |
| 2003/0194390 A1 | 10/2003 | Krall et al. |
| 2003/0203985 A1 | 10/2003 | Baldwin et al. |
| 2003/0206864 A1 | 11/2003 | Mangin |
| 2003/0215519 A1 | 11/2003 | Schwarz et al. |
| 2003/0233150 A1 | 12/2003 | Bourne et al. |
| 2004/0076582 A1 | 4/2004 | DiMatteo et al. |
| 2004/0092883 A1 | 5/2004 | Casey, III et al. |
| 2004/0096662 A1 | 5/2004 | Lanphere et al. |
| 2004/0101564 A1 | 5/2004 | Rioux et al. |
| 2004/0186377 A1 | 9/2004 | Zhong et al. |
| 2005/0025800 A1 | 2/2005 | Tan |
| 2005/0037047 A1 | 2/2005 | Song |
| 2005/0129775 A1 | 6/2005 | Lanphere et al. |

FOREIGN PATENT DOCUMENTS

| | | |
|---|---|---|
| DE | 3834705 | 4/1990 |
| DE | 94 14 868.6 | 2/1995 |
| DE | 297 24 255 U1 | 10/2000 |
| DE | 100 26 620 | 3/2002 |
| DE | 100 26 620 A 1 | 3/2002 |

| | | |
|---|---|---|
| EP | 0 067 459 A1 | 12/1982 |
| EP | 0 122 624 | 10/1984 |
| EP | 0 123 235 | 10/1984 |
| EP | 0 243 165 | 10/1987 |
| EP | 0 294 206 | 12/1988 |
| EP | 0 402 031 | 5/1990 |
| EP | 0 422 258 | 4/1991 |
| EP | 0 458 079 | 11/1991 |
| EP | 0 458 745 | 11/1991 |
| EP | 0 470 569 A1 | 2/1992 |
| EP | 0 547 530 B1 | 6/1993 |
| EP | 0 600 529 | 6/1994 |
| EP | 0 623 012 B1 | 11/1994 |
| EP | 0 706 376 B1 | 4/1996 |
| EP | 0 730 847 A1 | 9/1996 |
| EP | 0 744 940 B1 | 12/1996 |
| EP | 0 797 988 A2 | 10/1997 |
| EP | 0 067 459 B1 | 3/1998 |
| EP | 0 764 047 | 8/2003 |
| EP | 0 993 337 | 4/2004 |
| ES | 2 096 521 | 3/1997 |
| JP | 59-196738 | 11/1884 |
| JP | 62-45637 | 2/1987 |
| JP | 4-74117 | 3/1992 |
| JP | 6-57012 | 3/1994 |
| JP | 9-110678 | 4/1997 |
| JP | 9-165328 | 6/1997 |
| JP | 9-316271 | 12/1997 |
| JP | 10-130329 | 5/1998 |
| JP | 2000189511 | 7/2000 |
| JP | 2001079011 | 3/2001 |
| JP | 2002 017848 | 1/2002 |
| NZ | 255409 | 2/1997 |
| NZ | 517377 | 8/2003 |
| TW | 421658 | 2/2001 |
| WO | WO 91/12823 | 5/1991 |
| WO | WO 92/21327 | 12/1992 |
| WO | WO 93/00063 | 1/1993 |
| WO | WO 93/19702 | 10/1993 |
| WO | WO 94/10936 | 5/1994 |
| WO | WO 95/03036 | 2/1995 |
| WO | WO 95/22318 | 8/1995 |
| WO | WO 95/33553 | 12/1995 |
| WO | WO 96/37165 | 11/1996 |
| WO | WO 96/39464 | 12/1996 |
| WO | WO 98/04616 | 2/1998 |
| WO | WO 98/10798 | 3/1998 |
| WO | WO 98/26737 | 6/1998 |
| WO | WO 98/47532 | 10/1998 |
| WO | WO 99/00187 | 1/1999 |
| WO | WO 99/43380 | 2/1999 |
| WO | WO 99/12577 | 3/1999 |
| WO | WO 99/51278 | 10/1999 |
| WO | WO 99/57176 | 11/1999 |
| WO | WO 00/23054 | 4/2000 |
| WO | WO 00/32112 | 6/2000 |
| WO | WO 00/40259 | 7/2000 |
| WO | WO 00/71196 A1 | 11/2000 |
| WO | WO 00/74633 A2 | 12/2000 |
| WO | WO 01/12359 | 2/2001 |
| WO | WO 01/66016 | 9/2001 |
| WO | WO 01/70291 A2 | 9/2001 |
| WO | WO 01/72281 | 10/2001 |
| WO | WO 01/76845 | 10/2001 |
| WO | WO 01/93920 | 12/2001 |
| WO | WO 02/11696 A2 | 2/2002 |
| WO | WO 02/34298 A1 | 5/2002 |
| WO | WO 02/34299 A1 | 5/2002 |
| WO | WO 02/34300 A1 | 5/2002 |
| WO | WO 02/43580 A2 | 6/2002 |
| WO | WO 03/013552 | 2/2003 |
| WO | WO 03/016364 | 2/2003 |
| WO | WO 03/051451 | 6/2003 |
| WO | WO 03/082359 | 10/2003 |
| WO | WO 2004/019999 | 3/2004 |
| WO | WO 2004/040972 | 5/2004 |
| WO | WO 2004/073688 | 9/2004 |
| WO | WO 2004/075989 | 9/2004 |

OTHER PUBLICATIONS

"Contour® PVA Particles," Boston Scientific, http://www.bostonscientific.com, 2 pages (retrieved from the Internet on Sep. 6, 2005).

Hon et al., "Management of peripheral AVMs by embolotherapy using SAP-microsphere," *European Congress of Radiology*, Abstract 1024, http://www.ecr.org/conferences/ecr1997/sciprg/abs/9701024o.htm, 1 page (Retrieved from the Internet on Dec. 2, 2003).

Minamitani et al., "Embolization therapy of neoplastic lesions using a new embolic material without antineoplastic agents," *European Congress of Radiology*, Abstract 1499, http://www.ecr.org/conferences/ecr1997/sciprg/abs/9701499o.htm, 1 page (Retrieved from the Internet on Dec. 2, 2003).

Abbara et al., "Transcervical Expulsion of a Fibroid as a Result of Uterine Artery Embolization for Leiomyomata", *JVIR*, vol. 10, No. 4, pp. 409-411, 1999.

Abrahams, J.M. et al., "Topic Review: Surface Modifications Enhancing Biological Activity of Guglielmi Detachable Coils in Treating Intracranial Aneurysms", *Surg. Neurol.* 54:34-41, 2000.

Abrahams, J.M. et al., "Delivery of Human Vascular Endothelial Growth Factor with Platinum Coils Enhances Wall Thickening and Coil Impregnation in a Rat Aneurysm Model", *AJNR Am. J. Neuroradiol.* 22:1410-1417, Aug. 2001.

Ahuja, A.A., "Platinum Coil Coatings to Increase Thrombogenicity: A Preliminary Study in Rabbits", *AJNR Am. J. Neuroradiol.* 14:794-798; Jul./Aug. 1993.

Antibody Labeling, http://www.altcorp.com/AffinityLabeling/ablaeling.htm, pp. 1-6, May 20, 2003.

Barton, P. et al., "Embolization of Bone Metastases," *Journal of Vascular and Interventional Radiology*, 7(1):81-88 (Jan.-Feb. 1996).

Berkowitz, R.P. et al., "Vaginal Expulsion of Submucosal Fibroids After Uterine Artery Embolization", *Journal of Reproductive Medicine*, vol. 44, No. 4, pp. 373-376; Apr. 1999 http://www.reproductivemedicine.com.

Bourke et al., "Protein Drug Release from Photocrosslinked Poly(vinyl alcohol) Hydrogels," *Society for Biomaterials 28th Annual Meeting Transactions*, p. 144 (2002).

Bradley, E.A. et al., "Transcatheter Uterine Artery Embolisation to Treat Large Uterine Fibroids", *British Journal of Obstetrics and Gynaecology*, vol. 105, pp. 235-240; Feb. 1998.

Brockmann, J. et al., "Radiolabeling of p-Bz-DOTA-CD-11c antibody with $^{88}$Y: Conjugation, Labeling, Biodistribution studies", 2 pages, 2000 http://www.kernchemie.uni-mainz.de/downloads/jb2000/b14_brockmann.pdf.

Capozza et al., "Endoscopic treatment of vesico-ureteric reflux and urinary incontinence: technical problems in the paediatric patient," *British Journal of Urology*, 75(4):538-542 (Apr. 1995).

Carroll, B.A. et al., "Microbubbles as Ultrasonic Contrast Agents", *Investigative Radiology*, vol. 14, No. 3, p. 374, Supplement to May-Jun. 1979.

Carroll, B.A. et al., "Gelatin Encapsulated Nitrogen Microbubbles as Ultrasonic Contrast Agents", *Journal of Clinical and Laboratory Research*, vol. 15, No. 1, pp. 260-266, Feb. 1980.

Carstensen, E.L. et al., "Determination of the Acoustic Properties of Blood and its Components", *Journal of Acoustical Society of America*, vol. 25, No. 2, pp. 286-289, Mar. 1953.

Cirkel, U. et al., "Experience with Leuprorelin Acetate Depot in the Treatment of Fibroids: A German Multicentre Study", *Clinical Therapeutics*, vol. 14, Suppl. A, 1992.

Concentric Medical, Inc.- Product Information (3 pages), 2002.

Cruise et al., "In Vitro and In Vivo Characterization of a Hydrogel-Based Aneurysm Embolization System," *Society for Biomaterials 28th Annual Meeting Transactions*, p. 203 (2002).

Deasy, P. B., "*Microencapsulation and Related Drug Processes*", New York, NY, Marcel Dekker, Inc., 345 pages, 1984 (Table of Contents only).

DeGast, A.N. et al., "Transforming Growth Factor β-coated Platinum Coils for Endovascular Treatment of Aneurysms: An Animal Study", *Neurosurgery*, vol. 49, No. 3, pp. 690-696, Sep. 2001.

Duckwiler et al., "Catheters, embolic agents spark neurointervention," *Diagnostic Imaging*, 16(5):66-72 (May 1994).

Ersek et al., "Bioplastique: A New Textured Copolymer Microparticle Promises Permanence in Soft-Tissue Augmentation," *Plastic and Reconstructive Surgery*, 87(4):693-702 (Apr. 1991).

Eskridge, "Interventional Neuroradiology," *Radiology*, 172:991-1006 (Nov. 1989).

Feldman, L. et al., "Transcatheter Vessel Occlusion: Angiographic Results Versus Clinical Success", *Radiology*, vol. 147, pp. 1-5, Apr. 1983.

Ferrofluids, Physical Properties and Applications Ferrofluidics Corp., Nashua, NH, 5 pages, 1986.

FeRx Incorporated, FERX Profile http://www.biotechshares.com/FERX.htm, 4 pages (Retrieved from the internet on Jun. 26, 2003).

Fritzsch, T. et al., "SH U 508, A Transpulmonary Echocontrast Agent", *Investigative Radiology*, vol. 25, Supplement 1, pp. S160-S161, Sep. 1990.

Fujimoto, S. et al., "Biodegradable Mitomycin C Microspheres Given Intra-Arterially for Inoperable Hepatic Cancer", *Cancer*, vol. 56, pp. 2404-2410, 1985.

Gilbert, W.M. et al., "Angiographic Embolization in the Management of Hemorrhagic Complications of Pregnancy", *American Journal of Obstetrics and Gynecology*, vol. 166, No. 2, pp. 493-497, Feb. 1992.

Goldberg, B.B., "Ultrasonic Cholangiography", *Radiology*, vol. 118, pp. 401-404, Feb. 1976.

Gramiak et al., "Echocardiography of the Aortic Root," *Investigative Radiology*, 3(5):356-366 (Sep.-Oct. 1968).

Gramiak, R. et al., "Ultrasound Cardiography: Contrast Studies in Anatomy and Function", *Radiology*, vol. 92, No. 5, pp. 939-948, Apr. 1969.

Greenwood, L.H. et al., "Obstetric and Nonmalignant Gynecologic Bleeding: Treatment with Angiographic Embolization", *Radiology*, vol. 164, No. 1, pp. 155-159, Jul. 1987.

Gupta et al., "Plasma-induced graft polymerization of acrylic acid onto poly(ethylene terephthalate) films: characterization and human smooth muscle cell growth on grafted films," *Biomaterials*, 23:863-871 (2002).

Halstenberg et al., "Biologically Engineered Protein-*graft*-Poly(ethylene glycol) Hydrogels: A Cell Adhesive and Plasmin-Degradable Biosynthetic Material for Tissue Repair," *Biomacromolecules*, 3(4):710-723 (2002).

Hirano et al., "Transcutaneous Intrafold Injection For Unilateral Vocal Fold Paralysis: Functional Results," *Ann. Otol. Rhinol Laryngol.*, 99(8):598-604 (Aug. 1990).

"Injectable Tissue Implant Could Repair Ravages of Surgery", Clemson University, Biotech Week, Oct. 22, 2003, p. 117.

Jiaqi, Y. et al., "A New Embolic Material: Super Absorbent Polymer (SAP) Microsphere and Its Embolic Effects," *Nippon Acta Radiologica*, 56:19-24 (1996).

Jones, S.K. et al., "Experimental Examination of a Targeted Hyperthermia System Using Inductively Heated Ferromagnetic Microspheres in Rabbit Kidney", *Phys. Med. Biol.*, vol. 46, No. 2, pp. 385-398, Feb. 2001, www.iop.org/Journals/pb.

Jung et al., "Sulfobutylated poly(vinyl alcohol)-graft-poly(lactide-co-glycolide)s facilitate the preparation of small negatively charged biodegradable nanospheres," *Journal of Controlled Release*, 67:157-169 (2000).

Kallmes, D.F. et al., "In Vitro Proliferation and Adhesion of Basic Fibroblast Growth Factor-producing Fibroblasts on Platinum Coils", *Radiology*, vol. 206, No. 1, pp. 237-243, Jan. 1998.

Kerber, C., "Balloon Catheter with a Calibrated Leak", *Radiology*, vol. 120, pp. 547-550, Sep. 1976.

Khankan et al., "Embolic Effects of Superabsorbent Polymer Microspheres in Rabbit Renal Model: Comparison with Tris-acryl Gelatin Microspheres and Polyvinyl Alcohol," *Radiation Medicine*, 22(6):384-390 (2004).

Kim et al., "Poly(vinyl alcohol) beads with core-shell structure for drug delivery," *Cosmetic and Pharmaceutical Applications of Polymers*, Plenum Press, New York, pp. 209-214 (1991).

Kim et al., "Suspension polymerized poly(vinyl alcohol) beads for drug delivery," *Polymeric Materials: Science and Engineering, Proceedings of the ACS Division of Polymeric Materials: Science and Engineering*, 63:64-67 (1990).

Kochan, J.P. et al., "Interventional Neuroradiology: Current Practices and Techniques at Temple University Hospital," http://www.temple.edu/radiology/stroke.html, 5 pages.

Krinick et al., "A polymeric drug delivery system for the simultaneous delivery of drugs activatable by enzymes and/or light," *J. Biomater. Sci. Polymer Edn*, 5(4):303-324 (1994).

Kuhn, R. et al., "Embolic Occlusion of the Blood Supply to Uterine Myomas: Report of 2 Cases", *Aust. NZ. J. Obstet. Gynaecol.*, vol. 39, No. 1, pp. 120-122, Feb. 1999.

Kurbatova, G.T. et al., "Magnetically-guided Anesthetics Based on Highly Dispersed Iron Powders Coated by Polyacrylamide", *Biofizika*, vol. 47, No. 2, pp. 331-337, Mar.-Apr. 2002 http://intapp.medscape.com/px/medlineapp.

Laurent, "Materials and biomaterials for interventional radiology," *Biomed. & Pharmacother.*, 52:76-88 (1998).

Lemperle et al., "PMMA Microspheres for Intradermal Implantation: Part 1. Animal Research," *Annals of Plastic Surgery*, 26(1):56-63 (Jan. 1991).

Lendlein, A. et al., "Biodegradable, Elastic Shape-Memory Polymers for Potential Biomedical Applications", *Science*, vol. 296, pp. 1673-1676, May 31, 2002.

Leventon, William, "Hemocompatible Coatings for Blood-Contacting Devices", *Medical Device & Diagnostic Industry: Coating Technologies—New Methods to Ensure Blood Compatibility*, vol. 25, No. 8, pp. 62-67, Aug. 2003.

Levy et al., "Transcatheter Uterine Artery Embolization for the Treatment of Symptomatic Uterine Fibroid Tumors," *Journal of Women's Imaging*, 2(4):168-175 (2000).

Lipman, "Uterine artery embolization for the treatment of symptomatic uterine fibroids: A review," *Applied Radiology*, 29(7):15-20 (Jul. 2000).

Lowery, C.L. et al., "Screening Tests for Intrauterine Growth Retardation: A Comparison of Umbilical Artery Doppler to Real-Time Ultrasound", *Echocardiography*, vol. 7, No. 2, pp. 159-164, Mar. 1990.

Marich, K.W. et al., "Real-Time Imaging with a New Ultrasonic Camera: Part I, In Vitro Experimental Studies on Transmission Imaging of Biological Structures", *Journal of Clinical Ultrasound*, vol. 3, No. 1, pp. 5-16, Mar. 1975.

Markus et al., "Experimental Aspects of High-Intensity Transient Signals in the Detection of Emboli," *J. Clin. Ultrasound.*, 23(2):81-87 (Feb. 1995).

Maruhashi, "Modified Polyvinyl Alcohols I and II," *Polyvinyl Alcohol—Developments*, John Wiley & Sons, Chichester, England, pp. 160-161 and pp. 186-191 (1992).

Marx, W. F. et al., "Endovascular Treatment of Experimental Aneurysms by Use of Biologically Modified Embolic Devices: Coil-mediated Intraaneurysmal Delivery of Fibroblast Tissue Allografts", *AJNR. Am. J. Neuroradiol.*, vol. 22, pp. 323-333, Feb. 2001.

Mather, P.T., Research Group Homepage, Basic Goals and Methods, http://www.ims.uconn.edu/~mather, 4 pages.

Matsumoto, H. et al., "Basic Fibroblast Growth Factor Released from a Platinum Coil with a Polyvinyl Alcohol Core Enhances Cellular Proliferation and Vascular Wall Thickness: An In Vitro and In Vivo Study", *Neurosurgery*, vol. 53, No. 2, pp. 402-408, Aug. 2003.

Matsumoto, Y. et al., "Room-Temperature Ferromagnetism in Transparent Transition Metal-Doped Titanium Dioxide", *Science*, vol. 291, pp. 854-856, Feb. 2, 2001 www.sciencemag.org.

Mavligit, G. et al., "Gastrointestinal Leiomyosarcoma Metastatic to the Liver," *Cancer*, 75(8):2083-2088 (Apr. 15, 1995).

McIvor, J. et al., "Pregnancy After Uterine Artery Embolization to Control Haemorrhage from Gestational Trophoblastic Tumour", *British Journal of Radiology*, vol. 69, No. 823, pp. 624-629, Jul. 1996.

MerocelXL Sponge with Hytrol http://www.xomed.com/newproducts/merocelxl/merocelxl_earwick.asp, 3 pages, 2001.

Moroz, P. et al., "Arterial Embolization Hyperthermia in Porcine Renal Tissue", *Journal of Surgical Research*, vol. 105, No. 2, pp. 209-214, Jun. 15, 2002.

Moroz, P. et al., "Hepatic Clearance of Arterially Infused Ferromagnetic Particles", *Int. J. Hyperthermia*, vol. 19, No. 1, pp. 23-24, Feb. 2003, http://www.tandf.co.uk/journals.

Namiki, "Application of Teflon Paste for Urinary Incontinence—Report of 2 Cases," *Uro. Int.*, 39:280-282 (1984).

Orienti et al., "Crosslinked Polyvinylalcohol Hydrogels as Vehicles for Hydrophilic Drugs," *Arch. Pharm. Pharm. Med. Chem.*, 333:421-424 (2000).

Orsini, L. F. et al., "Pelvic Organs in Premencheal Girls: Real-Time Ultrasonography", *Radiology*, vol. 153, No. 1, pp. 113-116, Oct. 1984.

Pedley et at, "Hydrogels in Biomedical Applications," *British Polymer Journal*, 12:99-110 (Sep. 1980).

Phillips, D. R. et al., "Experience with Laparoscopic Leiomyoma Coagulation and Concomitant Operative Hysteroscopy", *J. Am. Assoc. Gynecol. Laparosc*, vol. 4, No. 4, pp. 425-533, Aug. 1997.

Pistel et al., "Brush-like branched biodegradable polyesters, part III Protein release from microspheres of poly(vinyl alcohol)-graft-poly(D,L-lactic-co-glycolic acid)," *Journal of Controlled Release*, 73:7-20 (2001).

Politano et al., "Periurethral Teflon Injection for Urinary Incontinence," *The Journal of Urology*, 111:180-183 (1974).

Poppe, W. et al., "Pregnancy after Transcatheter Embolization of a Uterine Arteriovenous Malformation", *Am. J. Obstet. Gynecol.*, vol. 156, No. 5, pp. 1179-1180, May 1987.

Progelhof et al., "Table 4.21. Properties of electrical insulating films (101)," *Polymer Engineering Principles: Properties, Processes, and Tests for Design*, Hanser Publishers, Munich, p. 383 (1993).

PVA Plus, AngioDynamics® Inc., "Reliable PVA Foam Formulated for Consistency and Controlled Delivery—Embolization Particles Ordering Information," www.angiodynamics.com, 2 pages (Aug. 2002).

Ravina, J.H. et al., "Advantage of Pre-Operative Embolization of Fibroids: About a Multicentric Set of 31 Cases", *Contracept. Fertil. Sex.*, vol. 23, No. 1, pp. 45-49, Jan. 1995 (abstract).

Ravina, J.H. et al., "Arterial Embolisation to Treat Uterine Myomata", *Lancet*, vol. 346, pp. 671-674, Sep. 9, 1995.

Ravina, J.H. et al., "Interest of Particulate Arterial Embolization in the Treatment of Some Uterine Myoma", *Bull. Acad. Natle. Med.*, vol. 181, No. 2, pp. 233-246, Feb. 4, 1997 (Summary).

Repa, I. et al., "Mortalities Associated with Use of a Commercial Suspension of Polyvinyl Alcohol," *Radiology*, 170(2):395-399 (Feb. 1989).

Rhine et al., "Polymers for Sustained Macromolecule Release: Procedures to Fabricate Reproducible Delivery Systems and Control Release Kinetics," *Journal of Pharmaceutical Sciences*, 69(3):265-270 (Mar. 1980).

Rump, A. et al., "Pharmacokinetics of Intraarterial Mitomycin C in the Chemoembolisation Treatment of Liver Metastases," *Gen. Pharmac.*, 27(4):669-671 (1996).

Schetky, "Shape-Memory Alloys," *Encyclopedia of Chemical Technology*, Third Edition, vol. 20, John Wiley & Sons, New York, pp. 726-736 (1982).

Schlief, R. et al., "Enhanced Color Doppler Echocardiography of the Left Heart After Intravenous Injection of a New Saccharide Based Agent in Humans", *Circulation*, vol. 82, No. 2, p. 28, Oct. 1990 (Abstract).

Schlief, R. et al., "Successful Opacification of the Left Heart Chamber on Echocardiographic Examination after Intravenous Injection of a New Saccharide Based Contrast Agent", *Echocardiography*, vol. 7, No. 1, pp. 61-64, Jan. 1990.

Schwarz et al., "The acoustic filter: An ultrasonic blood filter for the heart-lung machine," *J. Thorac. Cardiovasc. Surg.*, 104(6):1647-1653 (Dec. 1992).

Shafik, "Intraesophageal Polytef injection for the treatment of reflux esophagitis," *Surg. Endosc.*, 10:329-331 (1996).

Shape Shifters, http://www.sciam.com/tehbiz/0501scicit6.html, 3 pages, 2001.

Shung, K.K. et al., "Scattering of Ultrasound by Blood", *IEEE Transactions on Biomedical Engineering*, vol. BME-23, No. 6, pp. 460-467, Nov. 1976.

Sigelmann, R.A. et al., "Analysis and Measurement of Ultrasound Backscattering from an Ensemble of Scatters Excited by Sine-Wave Bursts", *Journal of Acoustical Society of America*, vol. 53, No. 4, pp. 1351-1355, Apr. 1973.

SIR-Spheres (Yttrium-90 Microspheres), pp. 1-12.

SIR-Spheres, Radioactive Implant (Yttrium-90 Microspheres), Sirex Medical, Inc., San Diego, CA, Nov. 6, 2000, pp. 1-15.

Sirtex Medical Limited—Product Description http://www.sirtex.com/?p=72, 3 pages (Retrieved from the internet on May 27, 2003).

Sirtex Medical Limited—Targeted Radiotherapy with SIR-Spheres http://www.sirtex.com/?p=57, 2 pages (Retrieved from the internet on May 27, 2003).

Siskin et al., "Pathologic Evaluation of a Spherical Polyvinyl Alcohol Embolic Agent in a Porcine Renal Model," *J. Vasc. Interv. Radiol.*, 14:89-98 (2003).

Skotland, T. et al., "In Vitro Stability Analyses as a Model for Metabolism of Ferromagnetic Particles (Clariscan™), a Contrast Agent for Magnetic Resonance Imaging", *J. Pharm. Biomed. Anal.*, vol. 28, No. 2, pp. 323-329, Apr. 15, 2002.

"Smart Sutures Tie Themselves", Apr. 26, 2002, http://www.sciam.com/article.cfm?articleID=00047706-121F-1CD0-B4A8809EC588, 2 pages.

Smith et al., "Evaluation of Polydimethylsiloxane as an alternative in the Endoscopic Treatment of Vesicoureteral Reflux," *The Journal of Urology*, 152:1221-1224 (Oct. 1994).

Smith, M.D. et al., "Left Heart Opacification with Peripheral Venous Injection of a New Saccharide Echo Contrast Agent in Dogs", *JACC*, vol. 13, No. 7, pp. 1622-1628, Jun. 1989.

Soppimath et al., "Controlled release of antihypertensive drug from the interpenetrating network poly(vinyl alcohol)-guar gum hydrogel microspheres," *J. Biomater. Sci. Polymer Edn*, 11(1):27-43 (2000).

Stancato-Pasik, A. et al., "Obstetric Embolotherapy: Effect on Menses and Pregnancy", *Radiology*, vol. 204, No. 3, pp. 791-793, Sep. 1997.

Stein, R. et al., "Targeting Human Cancer Xenografts with Monoclonal Antibodies Labeled Using Radioiodinated, Diethylenetriaminepentaacetic Acid-appended Peptides", *Clinical Cancer Research*, vol. 5, No. 10, pp. 3079-3087, Oct. 1999 (Supplement).

Strasnick et al., "Transcutaneous Teflon® Injection for Unilateral Vocal Cord Paralysis: An Update," *The Laryngoscope*, 101:785-787 (Jul. 1991).

Tamatani, S. et al., "Histological Interaction of Cultured Endothelial Cells and Endovascular Embolic Materials Coated with Extracellular Matrix", *J. Neurosurg.*, vol. 86, No. 1, pp. 109-112, Jan. 1997.

Thanoo, B. C. et al., "Preparation and Properties of Barium Sulphate and Methyl Iothalamate Loaded Poly(vinyl Alcohol) Microspheres as Radiopaque Particulate Emboli," *Journal of Applied Biomaterials*, 2:67-72 (1991).

Thelen, V.M. et al., "Catheter Embolisation of Metastasising Renal Carcinomas Using Butyle-2-cyano-acrylate", *Fortschr. Rontgenstr.*, vol. 124, No. 3, pp. 232-235, Mar. 1976.

Tian et al., "Design and synthesis of amphiphilic poly (ethylene glycol) derivatives as micellar drug delivery systems," *Polymer Preprints*, 43(2):719-720 (Fall 2002).

Toon, "Improving a Key Weapon Against Cancer," Research Horizons, pp. 11-12, Spring/Summer 2001.

Waltman, A.C. et al., "Technique for Left Gastric Artery Catheterization", *Radiology*, vol. 109, No. 3, pp. 732-734, Dec. 1973.

White, Jr., "Embolotherapy in Vascular Disease," *American Journal of Roentgenology*, 142:27-30 (Jan. 1984).

Widder, K.J. et al., "Selective Targeting of Magnetic Microspheres Containing Adriamycin: Total Remission in Yoshida Sarcoma-Bearing Rats", *Proceedings of the 16th Annual Meeting of American Society of Clinical Oncology*, May 26-27, 1980, San Diego, CA, p. 261.

Widder, K. et al., "Magnetic Microspheres: Synthesis of a Novel Parenteral Drug Carrier", *Journal of Pharmaceutical Sciences*, vol. 68, No. 1, pp. 79-82, Jan. 1979.

Winters et al., "Periurethral injection of collagen in the treatment of intrinsic sphincteric deficiency in the female patient," *The Urologic Clinics of North America*, 22(3):673-678 (Aug. 1995).

Wu, A.M., "Engineered Antibodies for Breast Cancer Imaging and Therapy," http://www.cbcrp.org/research/PageGrant.asp?grant_id=111, 3 pages, 1996.

Yamashita, Y. et al., "Transcatheter Arterial Embolization of Obstetric and Gynaecological Bleeding: Efficacy and Clinical Outcome", *British Journal of Radiology*, vol. 67, pp. 530-534, Jun. 1994.

Yoon et al., "Surface Immobilization of Galactose onto Aliphatic Biodegradable Polymers for Hepatocyte Culture," *Biotechnol. Bioeng.*, 78(1):1-10 (Apr. 5, 2002).

Zisch et al., "Covalently conjugated VEGF-fibrin matrices for endothelialization," *Journal of Controlled Release*, 72:101-113 (2001).

Ziskin, M.C. et al., "Contrast Agents for Diagnostic Ultrasound", *Investigative Radiology*, vol. 7, No. 6, pp. 500-505, Nov.-Dec. 1972.

Zou, Ying-hua, et al. "Experimental Canine Hapatic Artery Embolization with Polyvinyl Alcohol Microspheres," *Zhong Hua Fang-She Xue ZaZhi*, 23(6):330-332 (1989).

Zou, Ying-hua, et al. "Experimental Canine Hapatic Artery Embolization with Polyvinyl Alcohol Microspheres," Translation, *Zhong Hua Fang-She Xue ZaZhi*, 23(6):330-332 (1989).

Beaujeaux, R. et al., "Trisacryl Gelatin Microspheres for Therapeutic Embolization, II: Preliminary Clinical Evaluation in Tumors and Arteriovenous Malformations," *AJNR Am. J. Neuroradiol* 17:541-548, Mar. 1996.

Stridbeck, H. et al., "Collateral Circulation Following Repeated Distal Embolization of the Hepatic Artery in Pigs," *Invest Radiol* 1984;19:179-183.

Wright, K.C. et al., "Partial Splenic Embolization Using Polyvinyl Alcohol Foam, Dextran, Polystyrene, or Silicone," *Radiology* 142:351-354, Feb. 1982.

"Pulmonary artery pseudoaneuyrsm/aneurysm" Available Web Site: http://www.mamc.amedd.army.mil/williams/chest/vascular/paaneurysm/paaneyrysm.htm.

Bachtsi, A.R. et al., "An Experimental Investigation of Enzyme Release from Poly(vinyl alcohol) crosslinked Microspheres", *J. Microencapsulation*, vol. 12, No. 1, pp. 23-35; 1995.

Barr, J.D., et al.,"polyvinyl Alcohol Foam Particles Sizes and Concentrations Injectable through Microcatheters", *JVIR*, vol. 9, No. 1, pp. 113-118; 1998.

Barttinelli, L. et al., "New Class of Poly(vinyl alcohol) Polymrs as Column- Chromatography Stationary Phases for Candida Rugosa Lipase Isoforms Separation.", *J. Chromatogr A*, vol. 753, No. 1, pp. 47-55; 1996. Abstract. http://www.ncbi.nlm.nih.gov/entrez/query.fcgi?.

Berenstein, A. et al., "Catheter and Material Selection for Transarterial Embolization: Technical Considerations. II. Materials.", *Radiology*, vol. 132, No. 3, pp. 631-639; 1979.

Berenstein, A. et al., "Microembolization Techniques of Vascular Occlusion: Radiologic, Patohologic, and Clinical Correlation", *AJNR Am I Neuroradiol*, vol. 2, No. 3, pp. 261-267; 1981. Abstract, http://www.ncbi.nlm.nih.gov/entrez/query.fcgi?.

Bruix, J. et al., "Transarterial Embolization Versus Symptomatic Treatment in Patients With Advanced Hepatocellular Carcinoma: Results of a Randomized, Controlled Trial in a Single Institution", *Hepatology*, Jun. 1998, vol. 27, No. 6, pp. 1578-1583 Available Web Site: http://www.hepatitis-central.com/hcv/hcc/embolization/references.html.

Buhle, Jr. EL, "Re: Re: Hepatic Arterial Embolization", *UCLA Medicine Online* Available Web Site: http://www.meds.com/archive/mol-cancer/1996/msg00128.html.

Burczak, et al., "Long-term in vivo performance and biocompatibility of poly (vinyl alcohol) hydrogel macrocapsules for hybrid-type artificial pancreas", *Biomaterials*, vol. 17, No. 24, pp. 2351-2356, 1996, abs:: http://www.ncbi.nlm.nih.gov/entrez/query.fcgi?cmd=retrieve&db=PubMed&list_uids=89824..., pp. 1, 2002.

Burczak, et al., "Polymeric materials for biomedical purposes obtained by radiation methods. V. hybrid artificial pancreas", *Polim Med*, vol. 24, No. 1-2, pp. 45-55, 1994, abs: http://www.ncbi.nlm.nih.gov/entrez/query.fcgi?cmd=retrieve&db =PubMed&list_uids=7915..., pp. 1, 2002.

Choe, et al., "An experimental study of embolic effect according to infusion rate and concentration of suspension in transarterial particulate embolization", *Invest Radiol*, vol. 32, No. 5, pp. 260-270, 1997, abs: http://www.ncbi.nlm.nih.gov/entrez/query.fcgi?cmd=retrieve&db=PubMed&list_uids=9140745&dopt+Abs..., pp. 1, 2002.

Chuang et al., "Experimental Canine Hepatic Artery Embolization with Polyvinyl Alcohol Foam Particles", *Departments of Diagnostic Radiology and Veterinary Medicine*, The University of Texas, M.D. Anderson Hospital and Tumor Institute at Houston, Texas, pp. 21-25.

Clarian Health Methodist—Indiana Lions Gamma Knife Center, "Arteriovenous Malformation" Available Web Site: http://www.clarian.com/tyhealth/gammaknife/cond_arter.asp.

Colombo M, "Treatment of Hepatocellular Carcinoma", University of Milan, Inst Internal Med, Irccs Maggiore Res Unit Liver, Canc, Firc, Via Pace 9 1-20122 Milan, Italy Source: Journal of Viral Hepatitis, 1997;4:125-130 Available Web Site: http://home.texoma.net/~moreland/stats/hcc-9.html.

Derdeyn, et al., "Collagen-coated acrylic microspheres for embolotherapy: in vivo and in vitro characteristics", *American Journal of Neuroradiology*, vol. 18, No. 4, pp. 647-653, 1997, abs: http://www.ncbi.nlm.nih.gov/entrez/query.fcgi?cmd=retrieve&db=PubMed&list_uids=9127025&dopt=Abs..., pp. 1, 2002.

Derdeyn, et al., "Polyvinyl alcohol particle size and suspension characteristics", *American Journal of Neuroradiology*, vol. 16, pp. 1335-1343, 1995.

DiLuccio et al., "Sustained-Release Oral Delivery of Theophylline by Use of Polyvinyl Alcohol and Polyvinyl Alcohol-Methyl Acrylate Polymers", *Journal of Pharmaceutical Sciences*, Jan. 1994, vol. 83, No. 1, pp. 104-106.

Gander, et al., "Effect of polymeric network structure on drug release from cross-linked poly(vinyl alcohol) micromatrices", *Pharm Res*, vol. 6, No. 7, pp. 578-584, 1989, abs: http://www.ncbi.nlm.nih.gov/entrez/query.fcgi?cmd=retrieve&db=PubMed&list_uids=25080..., pp. 1, 2002.

Germano, et al., "Histopathological follow-up study of 66 cerebral arteriovenous malformations after therapeutic embolization with polyvinyl alcohol", *J Neurosurg*, vol. 76, No. 4, pp. 607-614, 1992, abs: http://www.ncbi.nlm.nih.gov/entrez/query.fcgi?cmd=retrieve&db=PubMed&list_uids=15452..., pp. 1, 2002.

Geschwind et al., "Chemoembolization of Liver Tumor in a Rabbit Model: Assessment of Tumor Cell Death with Diffusion-Weighted MR Imaging and Histologic Analysis", *Journal of Vascular and Interventional Radiology*, Dec. 2000, vol. 11, No. 10, pp. 1244-1255.

Gohel, et al., "Formulation design and optimization of modified-release microspheres of diclofenac sodium", *Drug Dev Ind Pharm*, vol. 25, No. 2, pp. 247-251, 1999, abs: http://www.ncbi.nlm.nih.gov/entrez/quety.fcgi?cmd=retrieve&db=PubMed&list_uids=10065360&dop=A..., pp. 1, 2002.

Goodwin, et al., "Overview of embolic agents and their indications", *Eleventh Annual International Symposium on Endovascular Therapy*, pp. 303-306, 1999.

Goodwin, et al., "Preliminary experience with uterine artery embolization for uterine fibroids", *Journal of Vascular and Interventional Radiology*, vol. 8, No. 4, pp. 517-526, 1997.

Grandfils, et al., "Preparation of poly (D,L) lactide microspheres by emulsion solvent evaporation, and their clinical implications as a convenient embolic material", *J Biomed Mater Res*, vol. 26, No. 4, pp. 467-479, 1992, abs: http://www.ncbi.nlm.nih.gov/entrez/query.fcgi?cmd=retrieve&db=PubMed&list_uids=1601900&dopt=Abs..., pp. 1, 2002.

Hamada, et al., "Embolization with cellulose porous beads, II: Clinical Trial", abs: http://www.ajnr.org/content/abstract/17/10/1901?ijkey=R.a2yRMietlXw, pp. 1-2, 2002.

Horak, et al., "Hydrogels in endovascular embolization. I. Spherical particles of poly (2-hydroxyethyl methacrylate) and their medico-biological properties".

Horak, et al., "Hydrogels in endovascular embolization. II. Clinical use of spherical particles", *Biomaterials*, vol. 7, 1986.

Huang, et al., "Percutaneous endovascular embolization of intracerebral arteriovenous malformations. Experience in 72 cases", *Chin Med J*, vol. 108, No. 6, pp. 413-419, 1995, abs: http://www.ncbi.nlm.nih.gov/entrez/query.fcgi?cmd=retrieve&db=PubMed&list_uids=75552..., pp. 1, 2002.

International Search Report for International Application No. PCT/US01/06981 (2 pages).

Jack, et al., "Radiolabeled polyvinyl alcohol particles: a potential agent to monitor embolization procedures", *Int J Rad Appl Instrum B*, vol. 13, No. 3, pp. 235-243, 1986, abs: http://www.ncbi.nlm.nih.gov/entrez/query.fcgi?cmd=retrieve&db=PubMed&list_uids=37712, pp. 1, 2002.

Joy C, et al., 1991, "Use of Preoperative Embolization in the Treatment of Vascular Metastatic Lesions of the Spine" Available Web Site: http://www.aaos.org/wordhtml/anmeet91/scipro/ppr472.htm.

Kai, et al., "The utility of the microcrystalline cellulose sphere as a particulate embolic agent: an experimental study", *American Journal of Radiology*, vol. 21, No. 6, pp. 1160-1163, 2000, or http://www.ajnr.org/cgi/content/full/21/6/1160, pp. 1-7, 2002.

Kan, et al., "In vivo microscopy of the liver after injection of lipiodol into the hepatic artery and portal vein in the rat", *Acta Radiologica*, vol. 30, pp. 419-425, 1989.

Kerber et al., "Polyvinyl Alcohol Foam: Prepackaged Emboli for Therapeutic Embolization", *American Journal Roentgenol*, Jun. 1978, vol. 130, pp. 1193-1194.

Kerber, "Flow-Controlled Therapeutic Embolization: A Physiologic and Safe Technique", *AJR*, Mar. 1980, vol. 134, pp. 557-561.

Kim, et al., "Composite poly(vinyl alcohol) beads for controlled drug delivery", *Pharm Res*, vol. 9. No. 1, pp. 10-16, 1992, abs: http://www.ncbi.nlm.nih.gov/entrez/query.fcgi?cmd=retrieve&db=PubMed&list_uids=1589392&dopt=Abs..., pp. 1, 2002.

Kurata, et al., "Preoperative embolization for meningiomas using PVA particles", *No Shinkei Geka*, vol. 20, No. 4, pp. 367-373, 1992, abs: http://www.ncbi.nlm.nih.gov/entrez/query.fcgi?cmd=retrieve&db=PubMed&list_uids=1570057&dopt=Abs..., pp. 1, 2002.

Kurosaki et al., "Evaluation of PVA-Gel Spheres as GI-Transit Time Controlling Oral Drug Delivery System", *Proceedings of the 19th International Symposium on Controlled Release of Bioactive Materials*, Jul. 26-31, 1992, Orlando, Florida, pp. 273-274.

Kusano, et al., "Low-dose particulate polyvinylalcohol embolization in massive small artery intenstinal hemorrahage. Experimental and clinical results", *Invest Radiol*, vol. 22, No. 5, pp. 388-392, 1987, abs: http://www.ncbi.nlm.nih.gov/entrez/query.fcgi?cmd=retrieve&db=PubMed&list_uids=34963..., pp. 1, 2002.

Labarre et al., "Complement activation by substituted polyacrylamide hydrogels for embolisation and implantation", *Biomaterials*, vol. 23, pp. 2319-2327, 2002.

Lammer, et al., "Transcatheteral embolization with polyvinyl alcohol—technic and experimental studies", *Rontgenblatter*, vol. 36, No. 1, pp. 10-14, 1983, abs: http://www.ncbi.nlm.nih.gov/entrez/query.fcgi?cmd=retrieve&db=PubMed&list_uids=6823530&dop=Abs..., pp. 1, 2002.

Latchaw et al., "Polyvinyl Foam Embolization of Vascular and Neoplastic Lesions of the Head, Neck, and Spine", *Radiology*, Jun. 1979, vol. 131, pp. 669-679.

Leung et al., "Determinants of Postembolization Syndrome after Hepatic Chemoembolization", *Journal of Vascular and Interventional Radiology*, Mar. 2001, vol. 12, No. 3, pp. 320-326.

Markoff, et al., "Uterine arteriovenous malformation successfully embolized with a liquid polymer, isobutyl 2-cyanoacrylate", pp. 659-660, 1999.

Matsumaru, et al., "Embolic materials for endovascular treatment of cerebral lesions", *J Biomater Sci Polym Ed*, vol. 8, No. 7, pp. 555-569, 1997, abs: http://www.ncbi.nlm.nih.gov/entrez/query.fcgi?cmd=retrieve&db=PubMed&list_uids=91953..., pp. 1, 2002.

Mid-America Interventional Radiological Society, "New Treatment for Uterine Fibroids Avoids Surgery" Available Web Site: http://www.mirs.org/fibroids.htm.

Nakabayashi, et al., "Evaluation of particulate embolic materials with MR imaging, scanning electron microscopy, and phase-contrast microscopy", *American Journal of Neuroradiology*, vol. 18, No. 3, pp. 485-491, 1997, abs: http://www.ncbi.nlm.nih.gov/entrez/query.fcgi?cmd=retrieve&db=PubMed&list_uids=90904..., pp. 1-2, 2002.

Nakstad, et al., "Embolization of intracranial arteriovenous malformations and fistulas with polyvinyl alcohol particles nad platinum fibre coils", *Neuroradiology*, vol. 34, No. 4, pp. 348-351, 1992, abs: http://www.ncbi.nlm.nih.gov/entrez/query.fcgi?cmd=retrieve&db.=PubMed&list_uids=15284..., pp. 1, 2002.

Nash, et al., "Modifications of polystyrenic matrices for the purification of proteins. II. Effect of the degree of glutaraldehyde-poly(vinyl alcohol) crosslinking on various dye ligand chromatography systems", *J Chromatogr A*, vol. 776, No. 1, pp. 55-63, 1997, abs: http://www.ncbi.nlm.nih.gov/entrez/query.fcgi?cmd=retrieve&db=PubMed&list_uids=92860..., pp. 1, 2002.

Nikishin LF et al., 1999, "Interventional radiology in diffuse toxic goiter", *European Congress of Radiology—ECR* 1999 Available Web Site: http://www.ecr.org/conferences/ecr1999/sciprg/abs/p090041.htm.

Ophir, et al., "Ultrasonic backscatter from contrast producing collagen microspheres", *Ultrasonic Imaging*, vol. 2, pp. 67-77, 1980.

Oregon Health Sciences University, "Fibroid Embolization" Available Web Site: http://www.uhmc.edu/dotter-fibroid.

Parker, et al., "A particulate contrast agent with potential for ultrasound imaging of liver", *Ultrasound in Medicine and Biology*, vol. 13, No. 9, pp. 555-566, 1987.

Pesant A.C. et al., 1997, "Dural fistulas involving the cavernous sinus: Treatment by embolization—7 cases", *European Congress of Radiology—ECR* 1997 Available Web Site: http://www.ecr.org/conferences/ecr1997/sciprg/abs/9703088p.htm.

Physicians' Desk Reference Family Guide to Women's Health, "Chapter 7—Common Disorders of the Reproductive System" Available Web Site: http://www.healthsquare.com/pdrfg/wh/chapters/wh1ch01.htm.

Pritchard, et al., "*Poly(Vinyl Alcohol)*: *Basic Properties and Uses*", London, England: Gordon and Breach Science Publishers.

Pryor J and Berenstein A., "Epistaxis (Nose-bleeds)" Available Web Site: http://www.wehealny.org/inn/Radiology/nosebleeds.html.

Purdy, et al., "Arteriovenous malformations of the brain: choosing embolic materials to enhance safety and ease of excision", *J Neurosurg*, vol. 77, No. 2, pp. 217-222, 1992, abs: http://www.ncbi.nlm.nih.gov/entrez/query.fcgi?cmd=retrieve&db=PubMed&list_uids=16250..., pp. 1-2, 2002.

Quisling, et al., "Histopathology analysis of intraarterial polyvinyl alcohol microemboli in rat cerebral cortex", *American Journal of Neuroradiology*, vol. 5, pp. 101-104, 1984.

Rajan et al., "Sarcomas Metastatic to the Liver: Response and Survial after Cisplatin, Doxorubicin, Mitomycin-C, Ethiodol, and Polyvinyl Alcohol Chemoembolization", *Journal of Vascular and Interventional Radiology*, Feb. 2001, vol. 12, No. 2, pp. 187-193.

Ramos, et al., "Tumor vascular signals in renal masses: detection with Doppler US", *Radiology*, vol. 168, No. 3, pp. 633-637, 1988.

Shafik, A., "Intraesophageal Polytef injection for the treatment of reflux esophagitis", *Department of Surgery and Experimental Research, Faculty of Medicine*, Cairo University, Cairo, Egypt, pp. 1-2, Received: Jun. 22, 1994; Accepted: Oct. 15, 1994 http://www.ahmedshafik.org/Group-D/d016.htm.

Spickler, et al., "The MR appearance of endovascular embolic agents in vitro with clinical correlation", *Comput Med Imaging Graph*, vol. 14, No. 6, pp. 415-423, 1990, abs: http://www.ncbi.nlm.nih.gov/entrez/query.fcgi?cmd=retrieve&db=PubMed&list_uids=21487..., pp: 1, 2002.

Spies JB, "Georgetown University Medical Center. Uterine Fibroid Embolization (UFE). An alternative to surgery for patients with uterine fibroids. Literature Review." Available Web Site: http://www.dml.georgetown.edu/fibroids.

Strunk, et al., "Treatment of congenital coronary arteriovenous malformations with microparticle embolization", *Cathet Cardiovasc Diagn*, vol. 22, No. 2, pp. 133-136, 1991, abs: http://www.ncbi.nlm.nih.gov/entrez/query.fcgi?cmd=retrieve&db=PubMed&list_uids=2009563&dop=Abs..., pp. 1, 2002.

Swanson DA et al., 1980, "The role of embolization and nephrectomy in the treatment of metastatic renal carcinoma", Urologic Clinics of North America 7(3):719-730, 1980. University of Pennsylvania Cancer Center—Oncolink. Available Web Site: http://www.oncolink.upenn.edu/pdg_html/cites/00/00585.html.

Tabata et al., "Tumor accumulation of poly(vinyl alcohol) of different sizes after intravenous injection", *Journal of Controlled Release*, Jan. 2, 1998, vol. 50, Nos. 1-3, pp. 123-133.

Tadavarthy et al., "Polyvinyl Alcohol (Ivalon) as an Embolizing Agent", *The American Journal of Roentgenology Radium Therapy and Nuclear Medicine*, Nov. 1975, vol. 125, No. 3, pp. 609-616.

Tadavarthy et al., "Polyvinyl Alcohol (Ivalon) as an Embolizing Agent", *Seminars in Interventional Radiology*, vol. 1, No. 2, Department of Radiology, University of Minnesota Hospitals, Minneapolis, Minnesota, Jun. 1984, pp. 101-109.

Tao, et al., "Study of microspheres for embolization of the hepatic artery", *Yao Xue Xue Bao*, vol. 23, No. 1, pp. 55-60, 1988, abs: http://www.ncbi.nlm.nih.gov/entrez/query.fcgi?cmd=retrieve&db=PubMed&list_uids=3400477&dop=A, pp. 1, 2002.

Tao, et al., "Study on embolization of hepatitic artery using microspheres", Acta Pharmaceutica Sinica vol. 23, No. 1, pp. 55-60; 1988. Translation.

Terada, et al., "Preoperative embolization of meningiomas fed by ophthalmic branch arteries", *Surg Neurol*, vol. 45, No. 2, pp. 161-166, 1996, abs: http://www.ncbi.nlm.nih.gov/entrez/query.fcgi?cmd=retrieve&db=PubMed&list_uids=86070..., pp. 1, 2002.

Thanoo, et al., "Controlled release of oral drugs from cross-linked polyvinyl alcohol microspheres", *J Pharm Pharmacol*, vol. 45, No. 1, pp. 16-20, 1993, abs: http://www.ncbi.nlm.nih.gov/entrez/query.fcgi?cmd=retrieve&db=PubMed&list_uids=8094438&dop=Abs..., pp. 1, 2002.

Thanoo, et al., "Tantalum loaded silicone micropsheres as particulate emboli", *J Microencapsul*, vol. 8, No. 1, pp. 95-101, 1991, abs: http://www.ncbi.nlm.nih.gov/entrez/query.fcgi?cmd=retrieve&db=PubMed&list_uids=1880697&dop=Abs..., pp. 1, 2002.

The Fibroid Embolization Center of the New York United Hospital Medical Center, "Fibroid Facts" Available Web Site: http://www.uhmc.com/fibro2.htm.

The Vanderbilt-Ingram Cancer Center, "Kidney Cancer." Available Web Site: http://www.mc.Vanderbilt.Edu/cancer/cancerinfo/kidney.html.

Tikkakoski, et al., "Preoperative embolization in the management of neck paragangliomas", *Laryngoscope*, vol. 107, pp. 821-826, 1997.

Touho, et al., "Intravascular treatment of spinal arteriovenous malformations using a microcatheter—with special reference to serial xylocaine tests and intravascular pressure monitoring", *Surgical Neurology*, vol. 42, No. 2, pp. 148-156. 1994, abs: http://www.ncbi.nlm.nih.gov/entrez/query.fcgi?cmd=retrieve&db=PubMed&list_uids=80912..., pp. 1, 2002.

UCLA Medical Group, "Uterine Embolization—Introduction—Statistics—Preservation of Fertility." Available Web Site: http://www.fibroids.org.

UCLA Radiological Sciences, "A summary of terms appearing in this text." Available Web Site: http://www.radsci.ucla.edu:8000/aneurysm/terms.html.

University Medical Center SUNY Stony Brook, Department of Urology, "Variococele and its treatment" Available Web Site:. http://www.hsc.sunysb.edu/urology/male_inf... variocoele_and_its_treatment.html.

Vivas S et al., "Arterioportal fistula and hemobilia in a patient with hepatic transplant", Gastroenterol Hepatol, Feb. 1998;21(2):88-9 Available Web Site: http://www.doyma.es/copiani/revistas/gastro/abstr/abs_p080.html.

Vogel F, "Nonsurgical Management of Uterine Fibroids" Available Web Site: http://www.holyname.org/brochure/fibroids.html.

Wakhloo, et al., "Extended preoperative polyvinyl alcohol microembolization of intracranial meningiomas: Assessment of two embolization techniques", *American Journal of Neuroradiology*, vol. 14, pp. 571-582, 1993.

Walker WJ, "Non Surgical Treatment of Fibroids in the UK by Uterine Artery Embolisation—An Alternative to Hysterectomy, Myomectomy and Myolysis" Available Web Site: http://www.fibroids.co.uk/thepaper.html.

Walsh RM et al., 1998, "Role of Angiography and Embolization for Acute Massive Upper Gastronintestinal Hemorrhage." Department of General Surgery and Radiology, Cleveland Clinic Foundation, Cleveland, Ohio. Available Web Site: http://www.ssat.com/98ddw/abstscorrt-47.html.

Wikholm G et al., 1996, "Embolization of Cerebral Arteriovenous Malformations: Part I—Technique, Morphology, and Complications", Departments of Neurology (CL) and Interventional Radiology (GW, PS), Sahlgrenska University Hospital, Goteborg, Sweden. Neurosurgery. Sep. 1996;39(3):448-57; discussion 457-9. Available Web Site: http://www.wwilkins.com/neurosurgery/0148-396X9-96inter.html.

Worthington-Kirsch RL, 1999, "Interventionalists offer management option for uterine fibroids." Diagnostic Imaging, pp. 47-49. Available Web Site: http://www.dimag.com/references/9903wortrefs.html.

Worthington-Kirsch, et al., "Uterine arterial embolization for the management of leiomyomas: Quality-of-life assessment and clinical response", *Radiology*, vol. 208, No. 3, 625-629, 1998.

Yamada, et al., "Extended intraarterial cisplatin infusion for treatment of gynecological cancer after alteration of intrapelvic blood flow and implantation of a vascular access device", *International Radiology*.

Yusi et al., "submuscosal Injection of Polyvinyl Alcohol in Artificially Created Vesico-Ureteral Reflux: A Preliminary Report," Asian J. Surg. 18(2): 122-127 (Apr. 1995).

\* cited by examiner

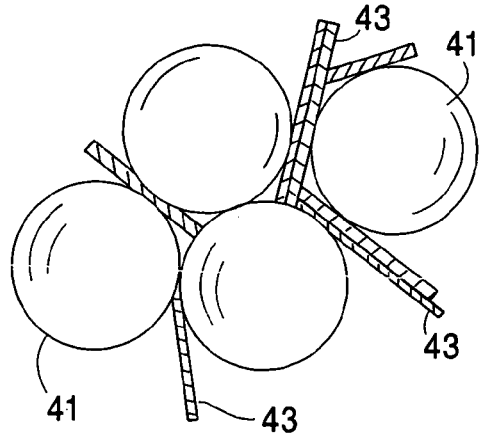
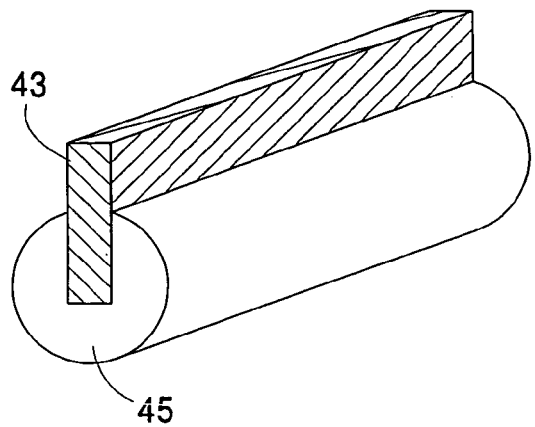
FIG. 4A
FIG. 4B
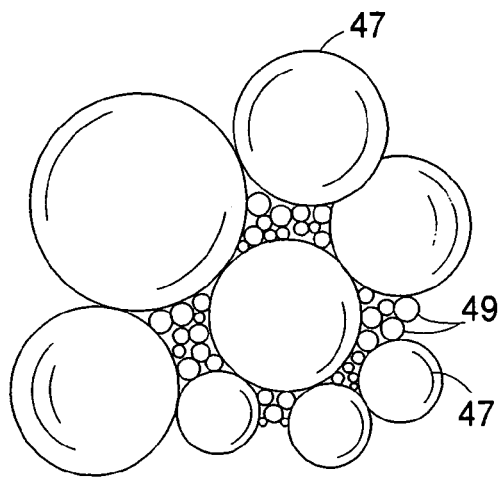
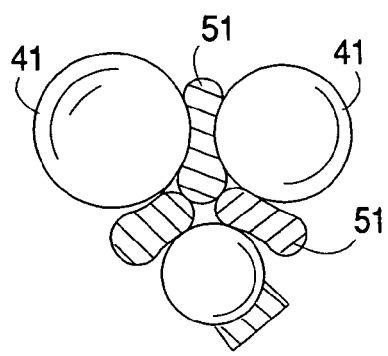
FIG. 5
FIG. 6

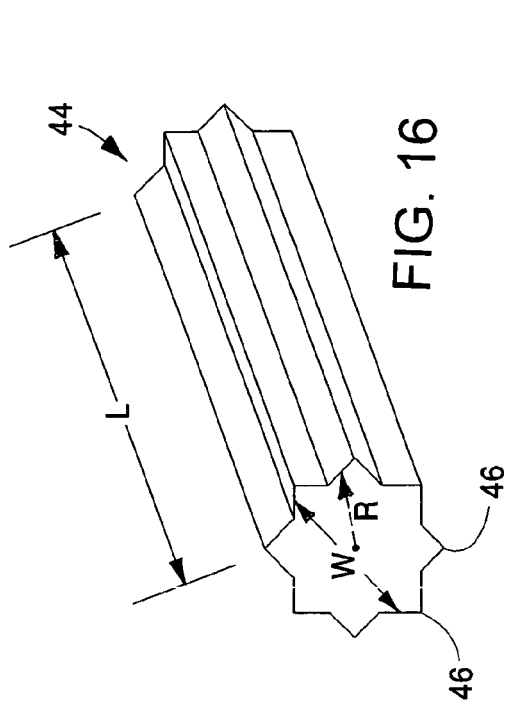
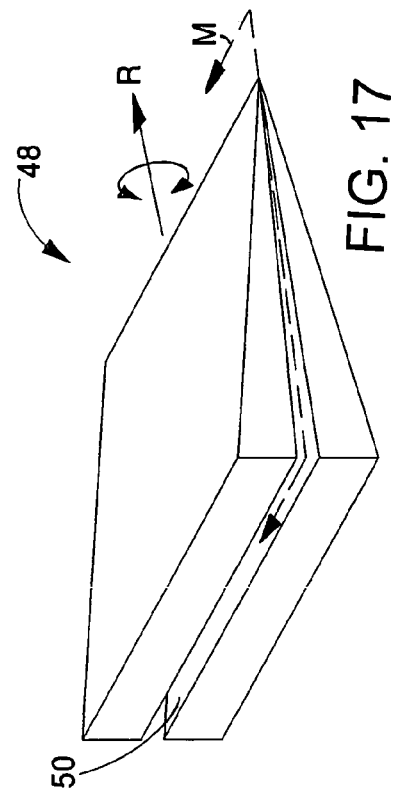
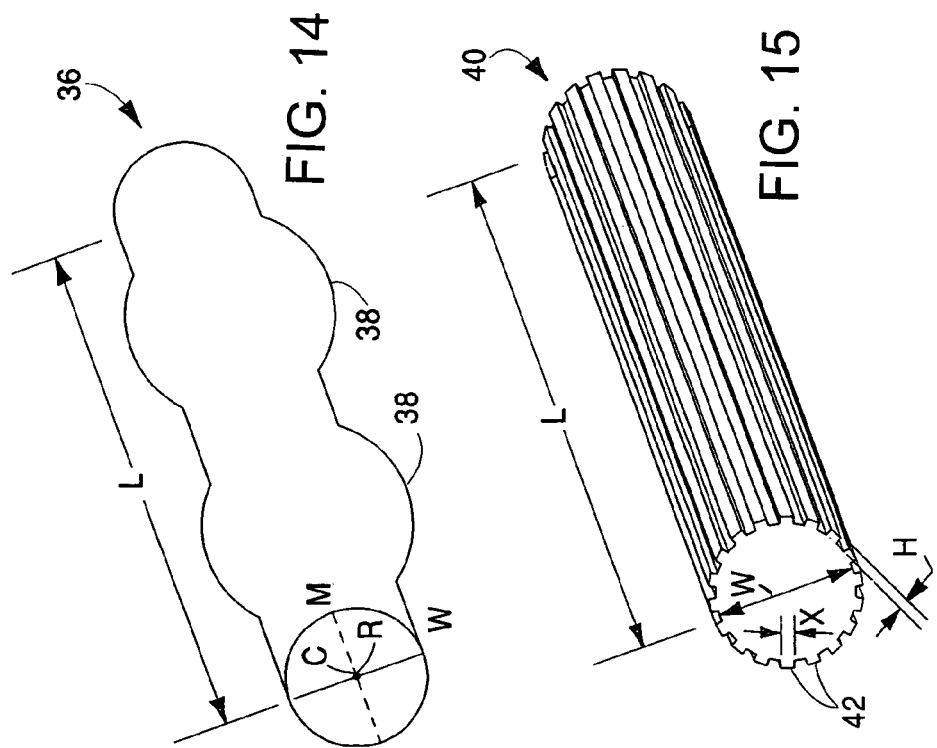

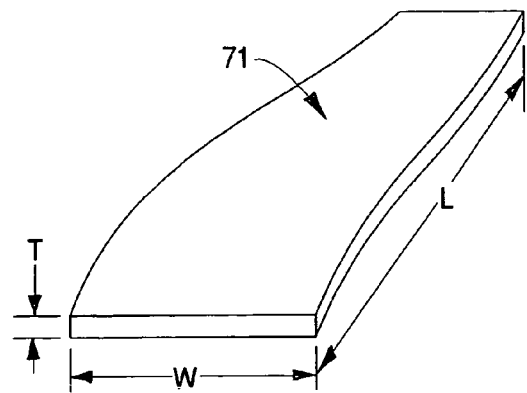 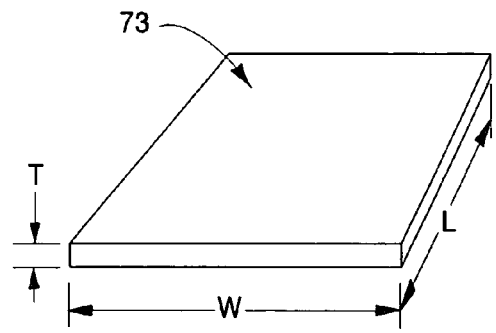
FIG. 18A　　　　　　　　　FIG. 18B
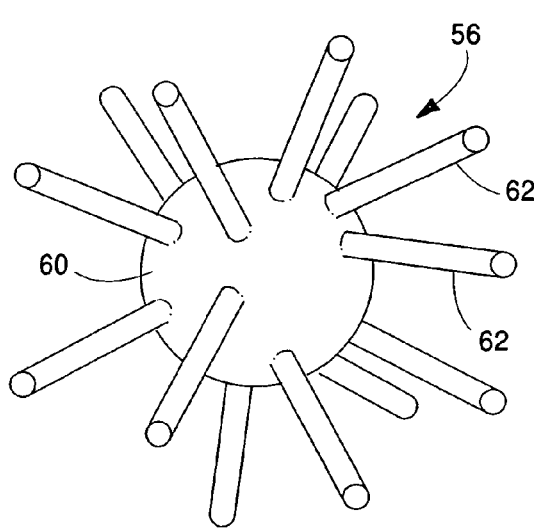 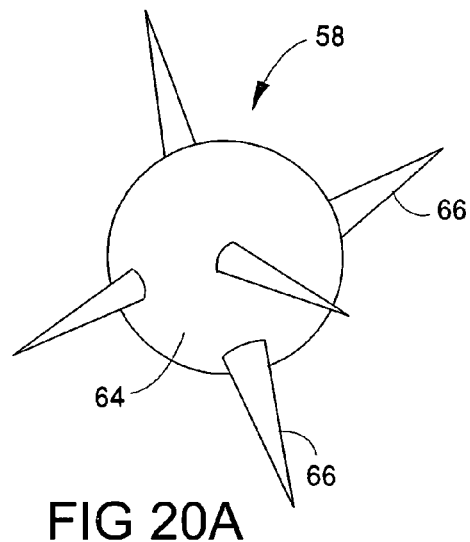
FIG. 19　　　　　　　　　FIG 20A

EMBOLIC COMPOSITIONS

CROSS-REFERENCE TO RELATED APPLICATIONS

This application is a continuation-in-part application of and claims priority to U.S. application Ser. No. 10/278,248, entitled "Mixing and Delivery of Therapeutic Compositions" and filed on Oct. 23, 2002, hereby incorporated by reference in its entirety. Also, this application is related to U.S. application Ser. No. 10/700,403, filed on the same day as this application.

TECHNICAL FIELD

The invention relates to embolic compositions.

BACKGROUND

Embolic compositions can be used to prevent or to treat certain conditions in the body. For example, in therapeutic vascular occlusions (sometimes called "embolizations"), particulate embolic compositions can be used to block, or occlude, vessels in the body. The embolic compositions can be used to block microvascular supplies of blood to tumors (thereby depriving the tumors of resources to grow), or to block hemorrhagic conditions in the body (thereby reducing or stopping bleeding). The compositions can be delivered to a target site using a catheter that has been introduced into the vessel.

SUMMARY

In one aspect, the invention features an embolic composition including a first collection of particles having a first common shape, and a second collection of particles having a second common shape different than the first common shape.

Embodiments may include one or more of the following features. The first common shape is substantially free of a concave region. The first common shape is substantially spherical. The second common shape is flake-like or strand-like. The second common shape includes a generally convex region. The second common shape includes an element extending from a non-fibrous base. The particles in the first collection and the particles in the second collection have different compositions. The first collection includes more particles than the second collection.

Alternatively or in addition, embodiments may include one or more of the following features. The particles of at least one of the collections can include a radiopaque material. The particles of at least one of the collections can include a portion capable of dissolving in a body. The particles of at least one of the collections can include a shape memory material and a non-shape memory material. The first collection of particles can include a shape memory material, and the second collection of particles includes a non-shape memory material. The particles of the first collection can be spherical, and the particles of the second collection can be non-spherical. The particles of the first and second collections can have different hardness. The particles of at least one of the collections can include a material capable of increasing in volume upon exposure to a predetermined stimulus. The first and second collections can be configured engage with each other. The first and second collections of particles can have different sizes. The first collection includes particles having a shape memory material.

The particles of at least one of the collections can include a therapeutic agent. The particles of only one collection can include the therapeutic agent. The particles in the first collection can include a first therapeutic agent, and the particles in the second collection can include a second therapeutic agent different than the first therapeutic agent. The particles of at least one of the collections can define a cavity, and include a therapeutic agent in the cavity.

In another aspect, the invention features an embolic composition including a first collection of particles having a first collection characteristic of shape or composition, and a second collection of particles having a second collection characteristic of shape or composition, wherein the first collection characteristic is different from the second collection characteristic.

Embodiments may include one or more of the following features. The first collection characteristic is the shape of the particles in the first collection. The second collection characteristic is the shape of the particles in the second collection. The particles in the first collection include a generally concave region. The particles in the second collection are substantially free of concave regions.

In another aspect, the invention features a kit including a first collection of particles having a first common shape, and a second collection of particles unblended with the first collection, the second collection having a second common shape different than the first common shape. The kit can further include a syringe and/or a catheter sized for insertion into a body.

In another aspect, the invention features a composition including a first embolic agent of a first phase, and a second embolic agent of a second phase different than the first phase. The first embolic agent can include solid embolic particles, a liquid, a gel, or a foam.

In another aspect, the invention features a method including introducing a first collection of particles having a first common shape into a body, and introducing a second collection of particles having a second common shape different than the first common shape into the body, the first and second collections occluding a site in the body.

Embodiments may include one or more of the following features. The collections are introduced into the body substantially simultaneously or sequentially. The collections are introduced from a catheter comprising two lumens, e.g., coaxial lumens. The method further includes exposing at least one collection of particles to a change in energy, e.g., temperature. The method further includes exposing at least one collection of particles to a predetermined material delivered through a catheter. The predetermined material is capable of changing the volume or shape of at least one collection of particles.

Other aspects, features and advantages of the invention will be apparent from the description of the preferred embodiments and from the claims.

DESCRIPTION OF DRAWINGS

FIG. 4A is an illustration of an embodiment of an occlusion; and FIG. 4B is an illustration of two embolic particles interlocking.

FIG. 5 is an illustration of an embodiment of an occlusion.

FIG. 6 is an illustration of an embodiment of an occlusion.

FIG. 14 is an illustration of an embodiment of an embolic particle having enlarged portions.

FIG. 15 is an illustration of an embodiment of an embolic particle having ridges.

FIG. 16 is an illustration of an embodiment of an embolic particle having a cross section with vertices.

FIG. 17 is an illustration of an embodiment of an embolic particle having a slot.

FIG. 18A is an illustration of an embodiments of a ribbon-like embolic particle; and FIG. 18B is an illustration of an embodiment of a sheet-like embolic particle.

FIG. 19 is an illustration of an embodiment of an embolic particle having fibers.

FIGS. 20A, 20B, 20C, 20D, 20E, and 20F are illustrations of embodiments of embolic particles having various projections.

FIG. 211B is a side view of the particle of FIG. 21A.

DETAILED DESCRIPTION

Figure 1:
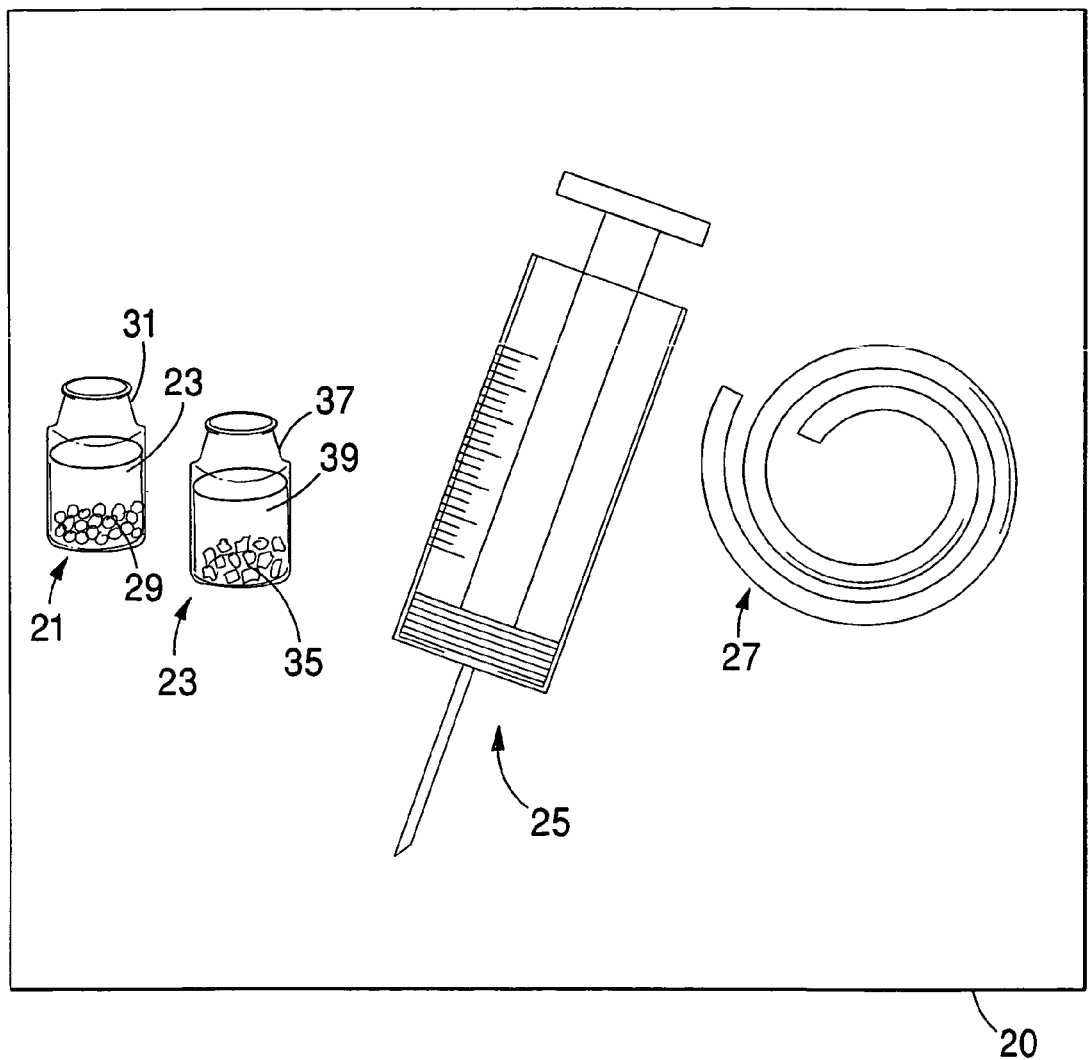
FIG. 1 is an illustration of an embodiment of an embolization kit.

Referring to FIG. 1, an embolization kit 20 includes a first embolic composition 21, a second embolic composition 23, a syringe 25, and a catheter 27 that is sized to be delivered to a body vessel. First embolic composition 21 includes a collection of embolic particles 29 (as shown, spherical particles) contained in a vessel 31 with a suitable carrier 33, such as saline. Second embolic composition 23 includes a collection of differently shaped embolic particles 35 (as shown, flake-like particles) contained in a vessel 37 with a suitable carrier 39. Spherical embolic particles are described, for example, in U.S. Ser. No. 10/215,594, filed Aug. 9, 2002, and are available as Contour SE™ Microspheres (polyvinyl alcohol (PVA) particles); and suitable flake-like embolic particles are available as Contour™ (irregularly shaped PVA particles), both available from Boston Scientific Corp., Natick, Mass. Syringe 25 and catheter 27 are used to deliver particles 29 and 35 from their respective vessels 31 and 37 to a target site in a body. Suitable syringes are described in, for example, U.S. Ser. No. 10/278,248.

Figure 2A:
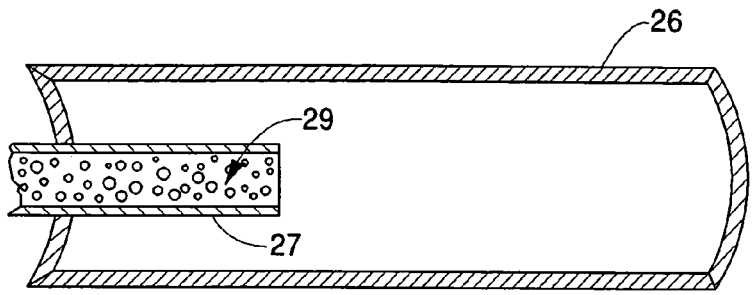
FIGS. 2A, 2B, 2C, 2D, and 2E illustrate an embodiment of a method of delivering an embolic composition.
Figure 2B:
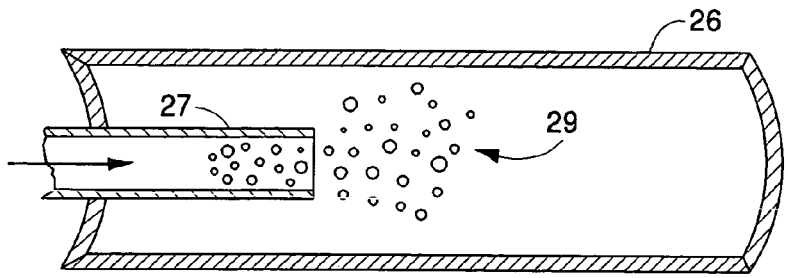
Figure 2C:
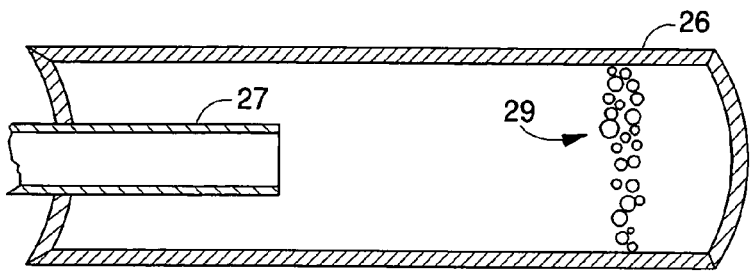
Figure 2D:
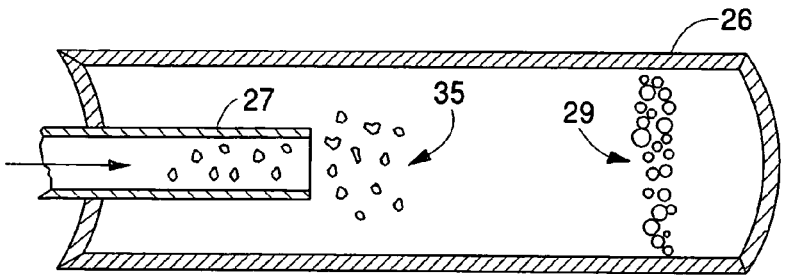
Figure 2E:
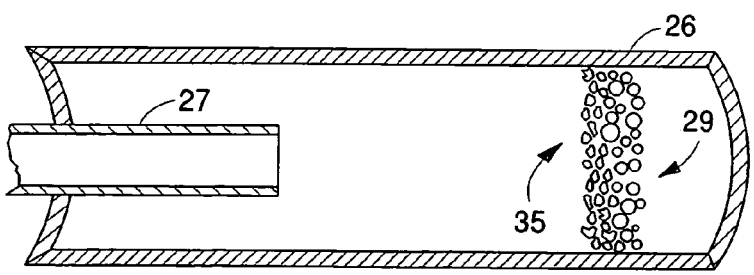
Figure 3A:
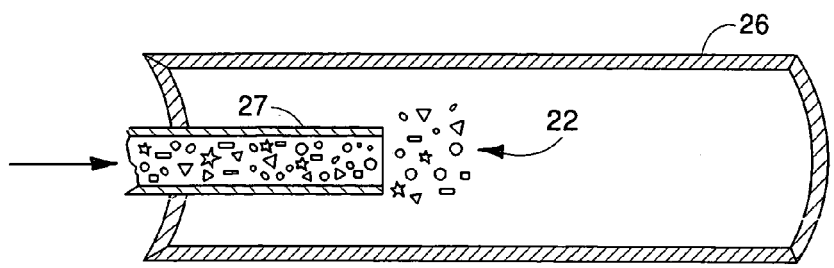
FIGS. 3A, 3B, and 3C illustrate an embodiment of a method of delivering an embolic composition.
Figure 3B:
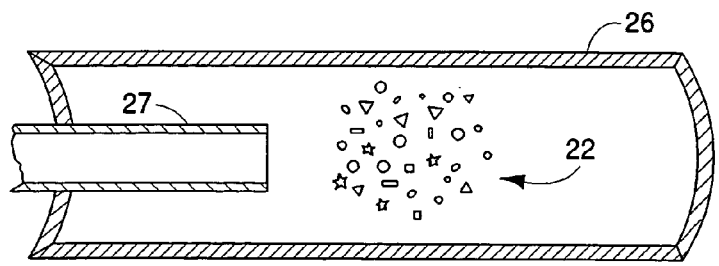
Figure 3C:
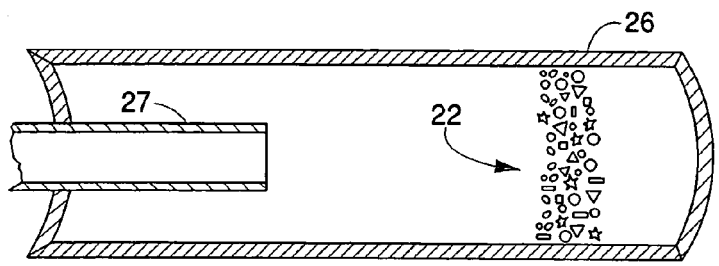

During use, particles 29 and 35 can be delivered to the body in a predetermined sequence or simultaneously. For example, referring to FIGS. 2A-2E, using syringe 25 spherical particles 29 are delivered through catheter 27, which has been emplaced in a body vessel 26. After particles 29 are released from catheter 27, the particles flow within vessel 26, aggregate, and block the vessel (FIG. 2C), thereby depriving a tumor or reducing hemorrhaging, for example. Subsequently, flake-like particles 35 are delivered through and released from catheter 27. Particles 35 can flow toward spherical particles 29 and fill or block any voids defined by the spherical particles, thereby enhancing embolization. In other embodiments, referring to FIGS. 3A-3C, collections of particles having different shapes (e.g., as described below) can be delivered simultaneously. As shown, particles 22 having rod-like shapes, star-like shapes, and spherical shapes are delivered at the same time. The differently shaped particles are capable of interacting synergistically (e.g., by engaging or interlocking) to form a well-packed occlusion, thereby enhancing embolization.

Other mixtures or combinations of different embolic particles can be used. For example, referring to FIG. 4A, three-dimensional particles 41, such as spheres and/or cylinders, can be introduced (before, after, or simultaneously) with two-dimensional particles 43, such as elongated, ribbon-like particles or flat particles. When the particles interact and aggregate, the ribbons or flat particles can fill the voids between the spheres, thereby providing a more effective occlusion. As another example, referring to FIG. 4B, ribbon-like particles 43 can be delivered with particles 45 having slots. The ribbon-like particles can interact (e.g., engage with or interlock with) the slots, thereby self-assembling to a more solid structure.

Alternatively or in addition, collections of particles of different sizes can be used together (e.g., sequentially or simultaneously). Referring to FIG. 5, relatively large particles 47 can be used to provide the general structure of an occlusion, while the smaller particles 49 can occupy the spaces between the large particles. The large and small particles can be delivered simultaneously or sequentially. For example, relatively large particles can be delivered first to form the general structure an occlusion, and relative small particles can subsequently be delivered to fill any spaces between the large particles.

Figure 7:
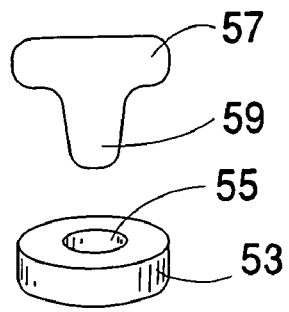
FIG. 7 is an illustration of two embolic particles having complementary features.
Figure 8A:
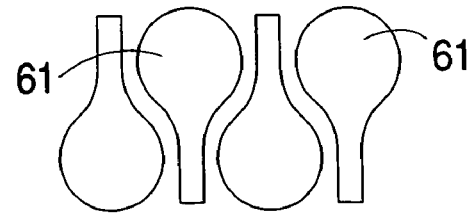
FIGS. 8A and 8B are illustrations of embodiments of embolic particles having teardrop shapes.
Figure 8B:
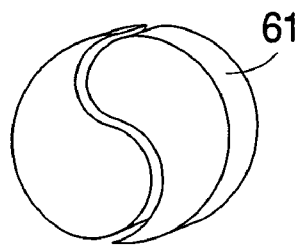
Figure 9A:
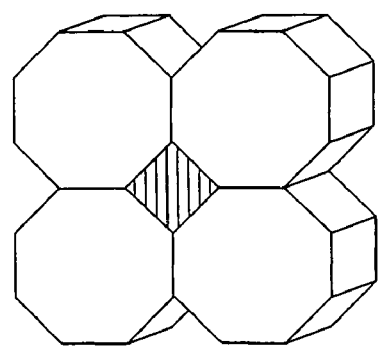
FIGS. 9A, 9B, and 9C are illustrations of embodiments of occlusions.
Figure 9B:
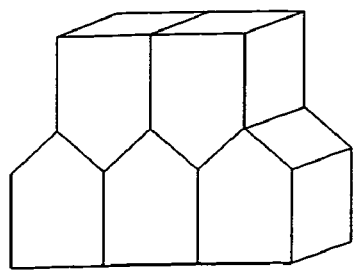
Figure 9C:
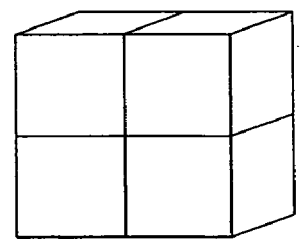

Other combinations including particles with complementary (e.g., interlocking) shapes are possible. For example, referring to FIG. 6, spherical particles 41 can be delivered with particles 51 having concave portions (e.g., oblate particles 52 described below) that receive portions of the spherical particles. Particles 51 are capable of filling voids between spherical particles 41. Other complementary particles capable of interlocking include particles 53 with openings 55, and particles 57 having a portion 59 (e.g., a projection) capable of penetrating the opening (FIG. 7). Other complementary particles 61 include those with teardrop shapes (FIGS. 8A and 8B) having a relatively small portion that extends curvilinearly to a relatively large portion. The particles can form relatively flat, two-dimensional structures, or three-dimensional structures (e.g., two particles can engage to form a sphere). In other embodiments, complementary particles have one or more surfaces that are relatively flat, i.e., planar. For example, the particles can be cubic or icosahedral particles. Referring to FIGS. 9A-9C, particles having flat surfaces can form occlusions by stacking like blocks in which the flat surfaces contact each other. The particles can be of similar or same size (e.g., FIG. 9B and 9C) or different size (e.g., FIG. 9A).

Alternatively or in addition, collections of particles having different physical and/or chemical properties can be used together (e.g., sequentially or simultaneously). For example, particles having different hardness (e.g., durometer) can be used together.

Collections of particles having different surface properties can be delivered together (e.g., sequentially or simultaneously). For example, hydrophobic particles can be surface modified with a dissolvable hydrophilic coating, and introduced together with unmodified hydrophobic particles. Since the modified and unmodified particles have different hydrophobicity/hydrophilicity, the particles tend not to aggregate. When the hydrophilic coating dissolves in the body to expose the hydrophobic surface, the particles can aggregate to form an occlusion. The particles can include a coating of a lubricious material, such as Glidex®, Mediglide® (silicone-based coatings), or Hydropass™ (water-based coatings) that enhance delivery of the particles (e.g., by preventing premature aggregation). The particles can include a coating of a material that changes upon exposure to a predetermined condition. For example, the coating material can include a hydrogel, alginate, or a starch that swells upon contact with a liquid, a change in temperature, and/or a change in pH. The soft, swollen coating can help the particles to easily deform and provide tight packing. The coating material can be soluble material, such as one that can dissolve in bodily fluids (described below) or another fluid subsequently delivered through the catheter. The soluble material can retard the transition of the shape memory material, for example, by acting as a thermal barrier. In embodiments in which the embolic particles include an absorbable material, the soluble material can delay absorption. An absorbable or bio-absorbable material is capable of dissolving upon exposure to bodily fluid at a known rate. Polymer coating materials which can be used as a bio-absorbable coating include gelatin; polylactic acid (e.g., poly-L-lactic acid, blends of DL-lactic acid, or poly(lactic acid-co-glycolic acid); polyglycolic acid; polysaccharides such as celluloses (e.g., hydroxymethylpropylcellulose), starches, dextrans, alginates and derivatives; and chlorohexidine gluconate, among others. The bio-absorbable coating thickness can be varied to regulate the amount of absorption, the type of bio-absorbable coating thickness can be varied to regulate the amount of absorption, and the type of bio-absorbable coating can be selected to absorb certain predetermined fluids, such as blood. The bio-absorbable material can also act as a matrix that encourages cell growth into an embolized vessel.

Other materials can be used. Suitable materials include, for example, polycarboxylic acids, cellulosic polymers, including cellulose acetate and cellulose nitrate, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polycaprolactone, polyhydroxybutyrate, polyhydroxybutyrate valerate and blends and copolymers thereof as well as other biodegradable, bioabsorbable and biostable polymers and copolymers. Coatings from polymer dispersions such as polyurethane dispersions (BAYHDROL®, etc.) and acrylic latex dispersions are also within the scope of the present invention. The polymer may be a protein polymer, fibrin, collage, and derivatives thereof, an extracellular matrix component, hyaluronic acid, chitosan, or another biologic agent or a suitable mixture of any of these. Other examples include polyacrylic acid, available as HYDROPLUS® (Boston Scientific Corporation, Natick, Mass.), and described in U.S. Pat. No. 5,091,205; polyisocyanates (e.g., such that the particles can become instantly lubricious when exposed to body fluids, see, for example, U.S. Pat. No. 5,091,205); polycaprolactone (e.g., a copolymer of polylactic acid and polycaprolactone, or copolymer of polycaprolactone and butylacrylate); tyrosine-derived polycarbonates and arylates; polyphosphazenes; polyiminocarbonates; polydimethyltrimethylcarbonates; biodegradable calcium phosphates (e.g., zinc calcium phosphates); cyanoacrylates; polydioxanone; polypropylene fumarate; polydepsipeptides; maleic anhydride copolymers; and anhydrous polyanhydrides.

In embodiments, collections of particles can include different therapeutic agents. The therapeutic agents can be released upon contact with bodily fluids. The soluble material described above can be used to control the release of the therapeutic agents. The agents can be negatively charged, cationically charged, amphoteric, or neutral. The therapeutic agents can be formed in the bulk of the particles or applied to the surfaces of the particles. For example, the surface of the particles can be textured, e.g., roughened. The textured surface can increase the surface area of the particles, thereby allowing more materials, such as a therapeutic agent, to be applied to the surface. The textured surface can provide pits or craters in which coating materials can be placed. Techniques for creating a textured surface include micrograzing, cryogenic pulverization, and/or microcracking.

Some examples of therapeutic agents are described in U.S. Ser. No. 10/232,265, filed Aug. 30, 2002, hereby incorporated by reference. Examples of other therapeutic agents include, but are not limited to, anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; anti-cancer agents or antineoplastic/antiproliferative/anti-miotic agents such as paclitaxel, 5-fluorouracil, cisplatin, vinblastine, vincristine, cladribine, epothilones, endostatin, angiostatin and thymidine kinase inhibitors; anesthetic agents such as lidocaine, bupivacaine, and ropivacaine; anti-coagulants such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promotors such as growth factor inhibitors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vascoactive mechanisms.

In embodiments, collections of particles can include different diagnostic agents. For example, alternatively or in addition to the surface modification, the internal structure of the embolic particles can be modified. The embolic particles can surround (e.g., encapsulate) a mass including a radiopaque material, a material that is visible by magnetic resonance imaging (MRI), and/or an ultrasound contrast agent. The materials or agent allows the particles to be tracked and monitored, e.g., by X-ray fluoroscopy, MRI, or ultrasound imaging. The radiopaque material (e.g., powder), MRI-visible material, and/or ultrasound visible material can be mixed with the material of the embolic particles, e.g., shape memory polymer, and formed into the particles. In some cases, the radiopaque material, MRI-visible material, and/or ultrasound visible material can be applied to the surface of the particles, for example, by compounding with one or more of the coating materials described above. Alternatively or in addition, the radiopaque material can be a mass placed in the particles. Examples of radiopaque materials include high-density metals, such as tantalum, tungsten, platinum, palladium, or gold.

Examples of MRI visible materials include non-ferrous metal-alloys containing paramagnetic elements (e.g., dysprosium or gadolinium) such as terbium-dysprosium, dysprosium, and gadolinium; non-ferrous metallic bands coated with an oxide or a carbide layer of dysprosium or gadolinium (e.g., $Dy_2O_3$ or $Gd_2O_3$); non-ferrous metals (e.g., copper, silver, platinum, or gold) coated with a layer of superparamagnetic material, such as nanocrystalline $Fe_3O_4$, $CoFe_2O_4$, $MnFe_2O_4$, or $MgFe_2O_4$; and nanocrystalline particles of the transition metal oxides (e.g., oxides of Fe, Co, Ni). Powder of MRI visible materials can be mixed with the material of the embolic particles, e.g., shape memory polymer.

The ultrasound contrast agent can be any material that enhances visibility during ultrasound imaging. An ultrasound contrast agent can include a suspension having trapped bubbles of sufficient size to deflect sound waves.

Figure 10:
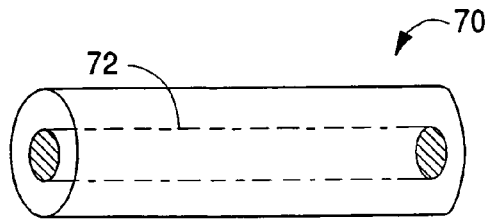
FIG. 10 is an illustration of an embodiment of an embolic particle having a cavity.

In other embodiments, referring to FIG. 10, an embolic particle 70 can be formed to define a cavity 72 in which a therapeutic agent can be placed and sealed. Cavity 72 can be sealed with a material that degrades or dissolves upon exposure to a predetermined condition, such as contact with bodily fluids, a change in pH, or a change in energy (e.g., temperature). When the sealant degrades or dissolves, the therapeutic agent can be released in the body. Suitable materials for sealing cavity 72 include polyvinyl alcohol (which dissolves in a solution having a selected pH, e.g., about >7.4), polyvinyl acetates, vinyl or collagen based glues or gelatins, and other degradable materials described above and in Buscemi et al., U.S. Pat. No. 5,443,495, hereby incorporated by reference. Embolic particle 70 can include a shape memory material and/or a non-shape memory material.

The embolic particles can be delivered with agents in different physical states. For example, the embolic particles can be delivered using a contrast agent (such as Omnipaque™ Renocal® or a radiopaque agent so that the delivery of the particles can be tracked. In embodiments in which the particles can absorb liquids, absorption of the contrast agent allows the particles to be monitored, e.g., after occlusion. The embolic particles can be delivered with liquid embolic materials (such as n-butyl cyanoacrylates (NBCA)), foam embolic materials (such as Ivalon® (PVA foam)), and/or gel embolics materials (such as hydrogels). NBCA is capable of polymerizing when contacted with an ionic substance, such as blood, saline ionic contrast media, and vessel epithelium. Polymerization time can be altered (e.g., prolonged) by adding varying amounts of glacial acetic acid and/or oil-based contrast agents, e.g., ethiodol or pantopaque. Other compositions capable of being introduced into the body as a liquid from which a solid thereafter precipitates are described in U.S. Pat. No. 6,575,896 and exemplified by Enteryx® (available from Boston Scientific Corp., Natick, Mass.). An example of a composition includes a biocompatible solvent (e.g., DMSO), a biocompatible polymer (e.g., cellulose acetate), and a contrast agent (e.g., barium sulfate). Other materials capable of solidifying in vivo include those used in polymer endoluminal paving and sealing (PEPS), described, for example, in U.S. Pat. No. 6,443,941. Still other examples include inorganic gels and other materials described in U.S. Pat. No. 6,296,632.

The embolic particles can be used with hemostatic agents. Agents include Gelfoam® (a gelatin sponge available from Upjohn Co., Kalamazoo, Mich.) and Avitene® (a microfibrillar collagen (e.g., 40-60 micron particles) available from Avicon Inc., Fort Worth, Tex.). Other examples include fibrin, fibrin glue, blood clotting precursors, other collagen-based agents (e.g., Collastat™, Superstat™, and Instat™), cellulose (e.g., Oxycel™ and Surgicel™), calcium alginate, hyaluronic acid, platelets, thrombin, and cryoprecipitate. In some cases, clotting can be promoted by charging the embolic particles, e.g., their surfaces. Other examples include silk sutures and microcoils (which can be used to build a framework or a mesh on which the particles can accumulate and occlude); fibered stainless steel (e.g., from Gianturco); platinum microcoils with or without Dacron® fibers (available from E.I. du Pont de Nemours and Co., and Target Therapeutics Boston Scientific); Guglielmi detachable coils (long, non-fibered platinum microcoils (available from Target Therapeutics Boston Scientific); and interlocking detachable coils. Alternatively or in addition, embolic therapy can include adding a vasospastic agent (such as serotonin and oxyhemoglobin) to constrict a blood vessel locally and to cause local occlusion and/or thrombus.

Figure 11A:
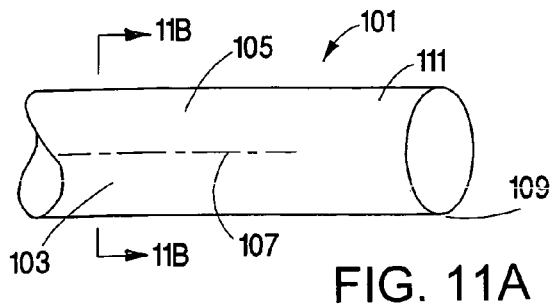
FIG. 11A is an illustration of an embodiment of a catheter.
Figure 11B:
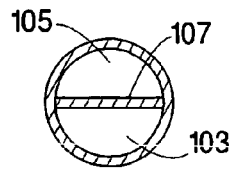
FIG. 11B is a cross-sectional view of the catheter of FIG. 11A, taken along line 11B-11B.
Figure 12A:
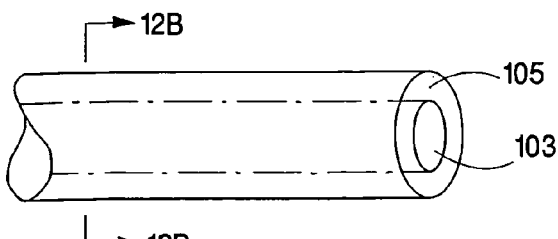
FIG. 12A is an illustration of an embodiment of a catheter.
Figure 12B:
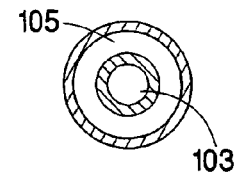
FIG. 12B is a cross-sectional view of the catheter of FIG. 12A, taken along line 12B-12B.

Mixtures of embolic particles can be delivered using a multi-lumen catheter and/or syringe. For example, referring to FIGS. 11A and 11B, a catheter 101 includes two lumens 103 and 105 separated by a wall 107. Wall 107 terminates proximally of the distal tip 109 of catheter 101, so at the distal tip, the catheter has a mixing chamber 111. During use, one type of embolic particles can be delivered through lumen 103, and another type of embolic particles can be delivered through lumen 105. Lumens 103 and 105 keep the particles separated so that, for example, they do not prematurely interact (e.g., aggregate or clog) inside catheter 101. The particles can then mix in chamber 111 before they are introduced into the body. In other embodiments, wall 107 terminates at distal tip 109, i.e., the catheter does not include a mixing chamber. Lumens 103 and 105 can be formed coaxially (FIGS. 12A and 12B), vis-à-vis, side-by-side, with or without a mixing chamber. The multi-lumen catheter or syringe can include more than two lumens, depending, for example, on the number of types of embolic particles to be delivered.

As described above, the embolic particles are not limited to spherical or flake-like particles. In other embodiments, the particles are formed in a variety of shapes that enhance aggregation, and numerous embodiments of embolic compositions and methods of delivering the compositions are possible. Any of the particles described herein can be used with any one or more other particle, in any combination.

In some embodiments, a collection of embolic particle includes particles having an elongated shape, as exemplified by the embodiments show in FIGS. 13A-17. That is, a particle has a length, L, that is greater than a width or diameter, W. The length, L, is the longest dimension of the particle, and can range from about 100 microns to about 1200 microns. For example, the length, L, can be greater than or equal to about 100, 200, 300, 400, 500, 600, 700, 800, 900, 1000, or 1100 microns; and/or less than or equal to about 1200, 1100, 1000, 900, 800, 700, 600, 500, 400, 300, or 200 microns. The width or diameter, W, is the average dimension taken along a plane transverse (e.g., orthogonal) to the direction of length, L. The width or diameter, W, can range from about 50 microns to about 1000 microns. For example, W can be greater than or equal to about 50, 100, 200, 300, 400, 500, 600, 700, 800, or 900 microns; and/or less than about 1000, 900, 800, 700, 600, 500, 400, 300, 200, or 100 microns. In some cases, the largest dimension of the particle is equal to or less than the smallest dimension of the instrument (e.g., microcatheter) used to deliver the particles.

Expressed another way, the embolic particle can have a length (L) to width/diameter (W) aspect ratio of greater than one. (A spherical particle would have a length to width aspect ratio of one.) In some embodiments, the particle has a length to width aspect ratio of from about 1.25:1 to about 10:1. For example, the aspect ratio can be greater than or equal to about 1.25:1, 2:1, 3:1, 4:1, 5:1, 6:1, 7:1, 8:1, or 9:1; and/or less than or equal to about 10:1, 9:1, 8:1, 7:1, 6:1, 5:1, 4:1, 3:1, or 2:1.

Figure 13A:
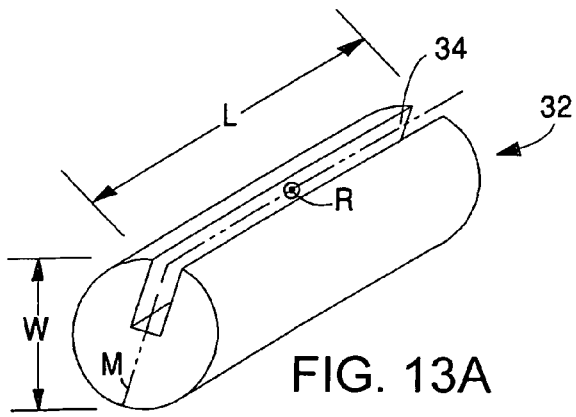
FIG. 13A is an illustration of an embodiment of an embolic particle having a slot.
Figure 13B:
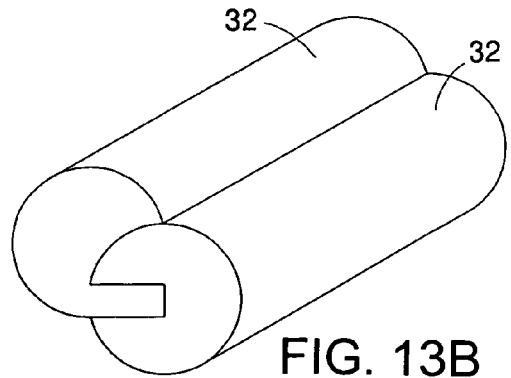
FIG. 13B is an illustration of two particles of FIG. 13A interlocking.

A collection of particles can include elongated particle having different shapes. For example, FIGS. 13A, 14, and 15 show different embodiments of elongated particles having a generally tubular shape. FIG. 13A shows an embolic particle 32 in the shape of a cylinder having a slot or a groove 34 extending along the length of the particle. As described below, in embodiments in which particle 32 includes a shape memory material, slot 34 allows particle 32 to be more easily compacted, e.g., for delivery, and facilitates interaction between the particles, e.g., by allowing the slots to engage (e.g., interlock) with each other and the particles to self-assemble (FIG. 13B). Slot 34 can extend the entire length of particle 32, or only a portion thereof. Particle 32 can include multiple slots 34, for example, the slots can be arranged collinearly along the particle, and/or distributed (symmetrically or asymmetrically) around the circumference of the particle. In some embodiments, particle 32 does not include slot 34, i.e., the particle can be a conventional cylinder.

FIG. 14 shows an embolic particle 36 in the shape of a cylinder having enlarged portions 38. In use, enlarged portions 38 help particles 36 to engage or mate with each other, thereby enhancing aggregation, e.g., by providing a more closely packed mass. Portions 38 are generally curvilinear or rounded portions having a diameter greater than the diameter of other portions of particle 36. In some embodiments, enlarged portions 38 have a maximum diameter of about 1,500 microns (e.g., less than about 1,200, 1,000, 800, 600, or 400 microns). Particle 36 can include one or more enlarged portions 38.

FIG. 15 shows an embolic particle 40 in the shape of cylinder having a plurality of ridges 42 extending along the length of the particle. As with slot 34 and enlarged portions 38, ridges 42 can help particles 40 engage or lock with each other during use. Ridges 42 can extend the entire length of particle 40, or only a portion thereof. Ridges 42 can be symmetrically or asymmetrically formed about the circumference of particle 40. In some embodiments, ridges 42 have a maximum height, H, of about 100 microns (e.g., less than about 100, 80, 60, or 40 microns), and a base width, X, of about 50 microns. Ridges 42 can have different cross-sectional shapes, such as square, rectangular, or triangular.

Indeed, as shown in FIGS. 13A and 14-17, a collection of embolic particles can have a variety of cross-sectional shapes. For example, FIGS. 13A and 14 show particles 32 and 36 having generally circular cross sections. FIG. 15 shows particle 40 having a generally gear-shaped cross section. FIG. 16 shows a star-shaped embolic particle 44 having a cross section with multiple (as shown, eight) vertices 46. In some embodiments, particle 44 can have one, two, three, four, five, six, seven, or more vertices 46, arranged symmetrically or asymmetrically around the particle. As another example, FIG. 17 shows an embolic particle 48 having a triangular cross section and a slot 50. Particle 48 further illustrates that the embolic particles can have uniform or non-uniform thickness, i.e., the particles can change dimensions, e.g., taper, along a particular direction. Particle 48, along with particles 40 and 44, also illustrate that the outer surface of the particles can be faceted, vis-à-vis cylindrical or rod-like (e.g., FIG. 13A). In other embodiments, the embolic particles can have other cross sectional shapes, for example, other non-circular shapes, such as oval, elliptical, or regularly or irregularly polygonal having 3, 4, 5, 6, 7, or 8 or more sides.

The embolic particles shown in FIGS. 13A and 14-17 also exemplify a class of embolic particles that can be characterized as having an element of symmetry. In comparison, a mass having a random shape typically does not include an element of symmetry. An example of an element of symmetry is a mirror plane, in which the structure of the particle is identical at corresponding, mirror-imaged locations on both sides of the plane. For example, particles 32 and 48 have a mirror plane (m) extending through the middle of slots 34 and 50, respectively (FIGS. 13A and 17). Particle 36 has an infinite number of mirror planes extending along the length of the particle and intersecting the cross-sectional center, C (FIG. 14). Particle 44 has numerous mirror planes, for example, extending along the length of the particle and intersecting the middle of a vertex 46, respectively (FIG. 16). Another example of an element of symmetry is an axis of symmetry about which rotation at selected (but not 360°) intervals yields the identical orientation. For example, particle 36 has an axis of symmetry, R, extending through the cross-sectional center about which rotation in any increment would yield the identical orientation (FIG. 14). Particle 44 also has an axis of symmetry, R, extending through the cross-sectional center about which rotation in 45° increments would yield the identical orientation (FIG. 16). Particles 32 and 48 have an axis of symmetry, R, about which rotation in 180 degrees increments would yield the identical orientation.

In addition, while the particles described above include certain discrete features (such as a slot, an enlarged portion, or a ridge), in some embodiments, an embolic particle can include multiple features, in any combination. For example, particle 36 with enlarged portions 38 can further include one or more slots and/or one or more ridges. Star-shaped particle 44 can include one or more slots and/or one or more enlarged portions. Wedged-shaped particle 48 may not include a slot, but can include, for example, one or more ridges. Any combination of features can be used to enhance interaction among the particles during use.

The particles in a collection of particles are also not limited to the relatively three-dimensional structures shown in FIGS. 13A and 14-17. In some embodiments, the embolic particles can be relatively two-dimensional. That is, the embolic particles can have a very small thickness. Referring to FIGS. 18A and 18B, in some cases, the particles are ribbon-like (particle 71) or sheet-like (particle 73). In embodiments in which the particles include a shape memory material, the flat morphology of the particles allows them to be initially compacted (e.g., folded) to facilitate delivery, and subsequently expanded (e.g., unfolded) upon exposure to a stimulus, as described below. In some embodiments, particles 71 or 73 have a thickness (T) less than about 50 microns (e.g., less than about 40, 30, or 20 microns). Alternatively or in addition, particles 71 or 73 have a thickness (T) to width (W) ratio of between about 1.25:1 and about 10:1. For example, the aspect ratio can be greater than or equal to about 1.25:1, 2:1, 3:1, 4:1, 5:1, 6:1, 7:1, 8:1, or 9:1; and/or less than or equal to about 10:1, 9:1, 8:1, 7:1, 6:1, 5:1, 4:1, 3:1, or 2:1. The length (L) of particles 71 and 73 can be as described above.

Figure 20B:
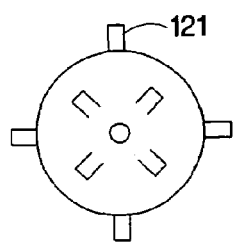
Figure 20C:
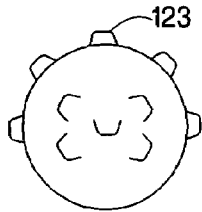

In some embodiments, a collection of embolic particles includes particles that are not substantially elongated. The particles can be generally spherical (e.g., completely spherical or egg-shaped) embolic particles (e.g., particles 56 and 58 shown in FIGS. 19 and 20A, described below). In embodiments in which the particles include a shape memory material, the generally spherical particles can be compacted to a generally oblate shape for delivery. Subsequently, the particles can be exposed to a stimulus (described below) that enlarges the particles, e.g., to the egg-shaped or spherical particles. Suitable dimensions for spherical embolic particles range from about one microns to about 1500 microns in diameter, and are described in U.S. Ser. No. 09/519,263, filed Mar. 6, 2000, hereby incorporated by reference.

Figure 21A:
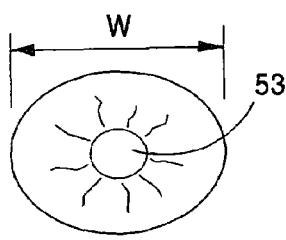
FIG. 21A is a top view of an embodiment of an oblate embolic particle.
Figure 21B:
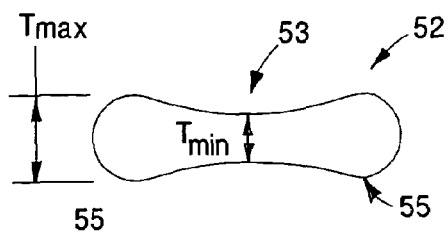
FIG. 21C shows the particle of FIG. 21A in a flexed position.
Figure 21C:
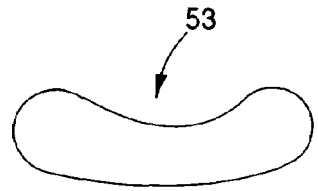

In other embodiments, the particles have a form that is generally oblate, e.g., like a red blood cell. Referring to FIGS. 21A-21B, an oblate particle 52 has a generally round or oval cross section and a relatively flat profile. The surface of particle 52 is generally curvilinear. At its central portion 53, the particle can be depressed, such that the central portion is narrowed, and the perimeter 55 of the particle is thicker than the central portion. As a result, particle 52 is concave at central portion 53, and convex at its perimeter 55. The oblate shape allows particle 52 to easily flex (FIG. 21C) so that the particle can be easily delivered, e.g., flow through a catheter without aggregating. In some embodiments, particle 52 can have a width (W) of about 50 to about 1200 microns (e.g., greater than or equal to about 50, 200, 400, 600, 800, or 1000 microns; and/or less than or equal to about 1200, 1000, 800, 600, 400, or 200 microns), a maximum thickness ($T_{max}$) of about 1000 to about 1200 microns (e.g., greater than or equal to about 1000 or 1100 microns; and/or less than or equal to about 1200 or 1100), and a minimum thickness ($T_{min}$) of about 100 to about 200 microns (e.g., greater than or equal to about 100 or 150 microns; and/or less than or equal to about 200 or 150 microns). In other embodiments, central portion 53 is not depressed, e.g., the thickness of the oblate particle is generally constant.

Figure 22A:
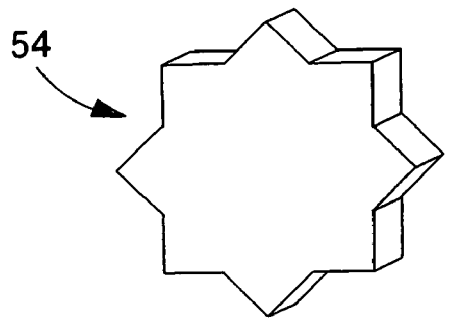
FIGS. 22A and 22B are illustrations of an embodiment of a star-shaped embolic particle.
Figure 22B:
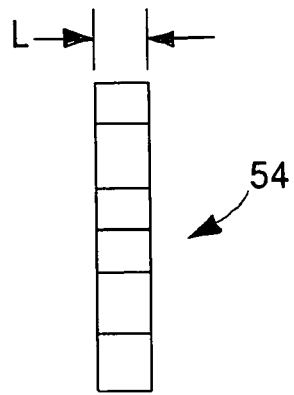
Figure 23A:
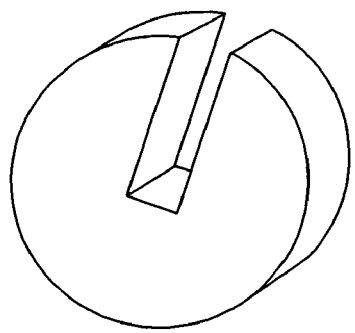
FIG. 23A is an illustration of an embodiment of an embolic particle having a slot.
Figure 23B:
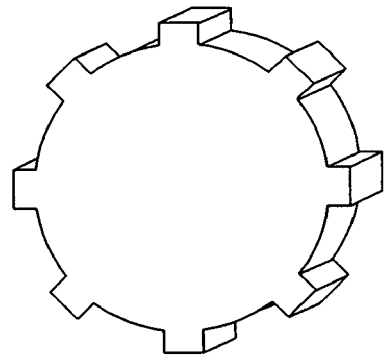
FIG. 23B is an illustration of an embodiment of a gear-shaped embolic particle.
Figure 23C:
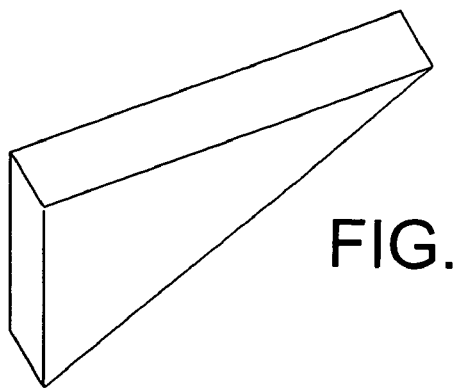
FIG. 23C is an illustration of an embodiment of an embolic particle.

Still other relatively non-elongated forms are possible. FIGS. 22A and 22B show a non-elongated embolic particle 54 having the generally star-shaped cross-section of particle 44, but without the extended length. The relatively short length can be less than about 100 microns (e.g., less than about 90, 80, 70, 60, 50, 40, 30, 20, or 10 microns). The cross-sectional shape of particle 54 can be modified similarly to the cross-sectional shape of particle 44. Similarly, particles 32, 40, and 48 (FIGS. 13A, 15, and 17) can be formed having the same cross-sections but without the extend lengths. FIGS. 23A, 23B, and 23C respectively show truncated embodiments of particle 32, particle 40, and particle 48 (without a slot).

A collection of particles (e.g., the particles shown in FIGS. 13A and 14-23C) can be formed wholly or in part of a biocompatible material. The performance of the particles can be enhanced by the particular set shape or shapes described herein. An example of a suitable material is a biocompatible polymer, such as polyvinyl alcohol (PVA) described in U.S. Ser. No. 10/215,594, filed Aug. 9, 2002. Other suitable materials include biocompatible ceramics, such as silica particles, described in U.S. Pat. No. 4,640,807 and EPO 067459, hereby incorporated by reference. Another type of material is an absorbable polymer. An absorbable polymer is a porous material that can absorb another material, such as a body fluid or a biocompatible agent, and expand from an initial (e.g., compacted) shape to a second (e.g., expanded) shape. Examples of absorbable polymers include hyaluronic acid (Medtronic® Xomed™, Inc., Minn.) and hydrogels. In some cases, the biocompatible material does not exhibit shape memory characteristics ("a non-shape memory material").

Mixtures of materials can be used to make the particles. For example, a particle can include a core made of a polymer, such as PVA, and an outer surface made of a ceramic, such as silica. The porous outer surface can be used to store materials, such as a radiopaque material or an MRI-visible material, and/or to release a material, such as a therapeutic agent. In other embodiments, the core includes a ceramic, and a polymer coating surrounds the core. The polymer can respond (e.g., changes shape) during use as described above.

As described above, in some embodiments, the embolic particles can include a shape memory material, which is capable of being configured to remember, e.g., to change to, a predetermined configuration or shape. The shape memory material is capable of transitioning between states and shapes based on exposure to environmental conditions, such as temperature, pH, or energy input, e.g., electromagnetic radiation. During delivery, the particles can be in the first state and can have a compacted shape that provides flowability to avoid clogging or aggregation, e.g., in the catheter. After the particles are released from the catheter, the particles are transitioned to the second state to form a second shape, such as an enlarged, non-compacted shape. The particles, in their second shape, then flow within the vessel, aggregate, and block the vessel. The shape memory material can provide a permanent occlusion, i.e., the occlusion is not substantially absorbed by the body and/or is not intended to be removed from the body. The particles can be formed at least in part or wholly of a shape memory material. Particles including a shape memory material can be used with particles that do not include a shape memory material.

The shape memory material can be, for example, a polymer or an alloy. Suitable shape memory polymers include elastomers that exhibit melt or glass transitions at temperatures that are above body temperature, e.g., at about 40 to 50° C., and safe for use in the body. Examples of polymers include shape memory polyurethanes (available from Mitsubishi), polynorbornene (e.g., Norsorex™ (Mitsubishi)), polymethylmethacrylate (PMMA), poly(vinyl chloride), polyethylene (e.g., crystalline polyethylene), polyisoprene (e.g., trans-polyisoprene), styrene-butadiene copolymer, rubbers, or photocrosslinkable polymer including azo-dye, zwitterionic and other photochromic materials (as described in *Shape Memory Materials*, Otsuka and Wayman, Cambridge University Press, 1998). Other shape memory polymers include shape memory plastics available from MnemoScience GmbH Pauwelsstrasse 19, D-52074 Aachen, Germany. Mixtures of polymeric shape memory materials can be used.

In some embodiments, the shape memory polymer is crosslinked and/or crystalline. The degree of crosslinking and/or crystallinity is sufficient to resist excessive creep or stress relaxation, e.g., after the polymer is heated. Crosslinking can also be controlled to adjust the melt or glass transition temperature and transition temperature range. In some cases, a narrow transition range, e.g. 10° C., 5° C., or less, is desirable. Crosslinking can be achieved by application of radiation, such as e-beam, UV, gamma, x-ray radiation, or by heat-activated chemical crosslinking techniques (e.g., with peroxides). In some radiation crosslinking techniques, the polymer need not be substantially heated to achieve crosslinking.

In some embodiments, the shape memory polymer is formed or set to a primary (e.g., stress free) shape during crosslinking. For example, an embolic particle can be crosslinked in a final shape. Subsequently, the polymer can be formed into a temporary shape, for example, by heating the polymer to a softening point (e.g., $T_m$ or $T_g$), deforming (e.g., compacting) the polymer, and cooling the polymer to below a softening point. When the polymer is subsequently heated to above the softening temperature, the polymer can recover to its primary form.

The shape memory material can be an alloy, such as a superelastic or pseudo-elastic metal alloy. An example of a superelastic materials include Nitinol™ (e.g., 55% nickel, 45% titanium), which can be heated and formed from a first shape to a second shape. When the Nitinol™ material is cooled, the material stays in the second shape. Subsequently, if the material is heated to a predetermined transition temperature, the material can transition to the first shape. Other examples of superelastic materials include silver-cadmium (Ag—Cd), gold-cadmium (Au—Cd), gold-copper-zinc (Au—Cu—Zn), copper-aluminum-nickel (Cu—Al—Ni), copper-gold-zinc (Cu—Au—Zn), copper-zinc/(Cu—Zn), copper-zinc-aluminum (Cu—Zn—Al), copper-zinc-tin (Cu—Zn—Sn), copper-zinc-xenon (Cu—Zn—Xe), iron beryllium ($Fe_3Be$), iron platinum ($Fe_3Pt$), indium-thallium (In—Tl), iron-manganese (Fe—Mn), nickel-titanium-vanadium (Ni—Ti—V), iron-nickel-titanium-Cobalt (Fe—Ni—Ti—Co) and copper-tin (Cu—Sn). See, e.g., Schetsky, L. McDonald, "Shape Memory Alloys", Encyclopedia of Chemical Technology (3rd ed.), John Wiley & Sons, 1982, vol. 20. pp. 726-736 for a full discussion of superelastic alloys. The shape memory alloy can be coated with a polymer, which may or may not have shape memory properties.

Mixtures of shape memory materials can be used to make a particle. For example, a particle can include a relatively hard core (e.g., made of Nitinol™) and a relatively soft outer surface (e.g., made of a polymer). The soft outer surfaces allow the particles to deform slightly, thereby enhancing packing when the particles aggregate.

A variety of techniques can be used to form the embolic particles. Examples of suitable techniques include microelectromechanical (MEM) techniques, micromachining, nanomachining, nanoetching, and/or nanoassembly. The particles can be formed by extrusion (e.g., of elongated particles), molding, and/or by stamping a sheet of shape memory material (e.g., having a thickness equal to the length of the particles).

The particles can be sterilized by a low temperature technique such as electron-beam irradiation, and packaged, e.g., about 1 to 5 ml of particles in about 5 to 10 ml saline. In embodiments, electron beam irradiation can be used to pharmaceutically sterilize the particles to reduce bioburden. In e-beam sterilization, an electron beam is accelerated using magnetic and electric fields, and focused into a beam of energy. This resultant beam can be scanned by means of an electromagnet to produce a "curtain" of accelerated electrons. The accelerated electron beam penetrates the collection of embolic particles to confer upon them electrons that destroy bacteria and mold to sterilize and reduce the bioburden in the embolic particles. Electron beam sterilization can be carried out by sterilization vendors such as Titan Scan, Lima, Ohio.

In use, the embolic particles can be delivered to an intended site by, for example, passing the particles through a catheter emplaced near the intended site. In embodiments in which the particles include a shape memory material, the particles are typically carried by a biocompatible solution having a temperature less than the transition temperature to inhibit the shape memory material from transitioning.

The particles can be selectively transitioned from a first state to the second state by exposing the particles to a predetermined stimulus or trigger. The transition of the shape memory material from its temporary configuration to its final configuration can be effected, for example, using a catheter carrying a heating device, such as a resistive heater or radiofrequency (RF) heater provided in the interior of the catheter. Alternatively or in addition, the shape memory material can be compounded to include a material, such as magnetic particles, that is susceptible to heating by magnetic effects, such as hysteresis effects. A magnetic field can be imposed on the particles by a source on a catheter or outside the body. Suitable magnetic particles are available as the Smartbond™ System from Triton Systems, Inc., Chelmsford, Mass. Heating by magnetic effects is discussed in U.S. Pat. No. 6,056,844, hereby incorporated by reference. Other methods for effecting the transition of the shape memory material include introducing an interactive or reactive material, such as a fluid through the catheter, into the body after the particles are released from the catheter. For example, the fluid can be heated to the transition temperature (e.g., about 30-60° C.) and/or have a predetermined pH to effect the transition. In other embodiments, a change in energy (e.g., temperature) can be produced by passing an optic fiber through the catheter to deliver optical energy, such ultraviolet or infrared radiation.

In other embodiments, a collection of embolic particles can be formed of a combination of a shape memory material and a non-shape memory material. For example, referring again to FIG. 19, particle 56 can include a generally spherical body 60 made of a non-shape memory material, and a plurality of fibers or filaments 62 made of a shape memory material extending from the surface of the body. In some cases, fibers 62 are formed such that the fibers have a free end exposed (as shown in FIG. 19); in other cases, the ends of the fibers are embedded in body 60 such that the fibers form a loop extending from the body. Since fibers 62 are made of a shape memory material, particle 56 can be compacted by folding the fibers to body 60 during delivery of the embolic composition, thereby enhancing delivery. Subsequently, fibers 62 can be unfolded in the body so that particles 56 can interact (e.g., tangle) with other and aggregate. In other embodiments, body 60 includes a shape memory material and fibers 62 include a non-shape memory material. The non-shape memory material can be as described above and can further include synthetic materials, such as polyester, nylon, DACRON®, PTFE, polypropylene, Kevlar®, natural materials, such as silk, collagen, or hair; alginate; or suture-based materials. Particle 56 can be formed wholly of a shape memory material or a non-shape memory material.

Figure 20D:
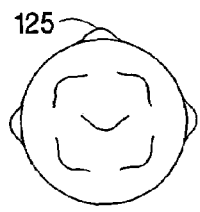
Figure 20E:
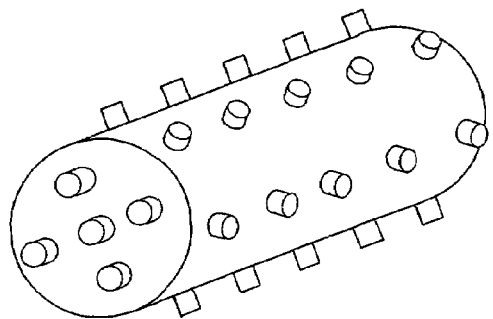
Figure 20F:
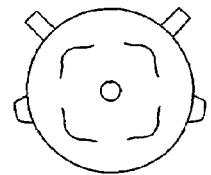

As another example, referring again to FIG. 20A, particle 58 includes a generally spherical body 64 and a plurality of spikes 66 (not drawn to scale) extending from the body. Body 64 can be formed of a non-shape memory material, and spikes 66 can be formed of a shape memory material. Like fibers 62, during use, spikes 66 can be folded and subsequently unfolded. Spikes 66 can have a length of about 100 microns. In other embodiments, body 64 is formed of a shape memory material, and spikes 66 are formed of a non-shape memory material. Particle 58 can be formed wholly of a shape memory material or a non-shape memory material. In other embodiments, projections other than spikes 66 can be used. For example, the projections can include rods 121 (FIG. 20B), frustoconical projections 123 (FIG. 20C), or bumps 125 (FIG. 20D). The projections can be evenly or unevenly distributed about a particle. The projections can be formed, wholly or in selected portions, of any of the embodiments of particles described herein, such as particles 32, 36, 40, 44, 48, or 120 (FIG. 20E). Different types of projections (e.g., rods and bumps), in any combination, can be formed on a particle (e.g., FIG. 20F).

Figure 24A:
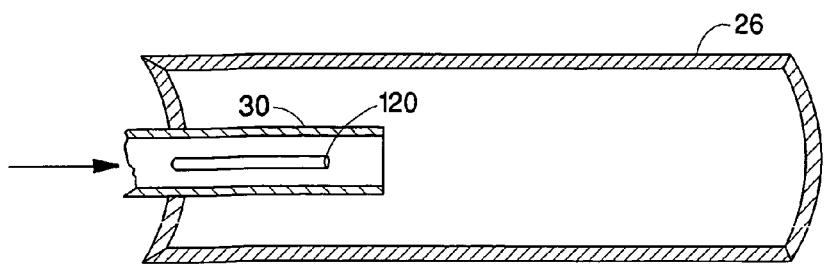
FIGS. 24A, 24B, and 24C illustrate an embodiment of a method of delivering an embolic composition.
Figure 24B:
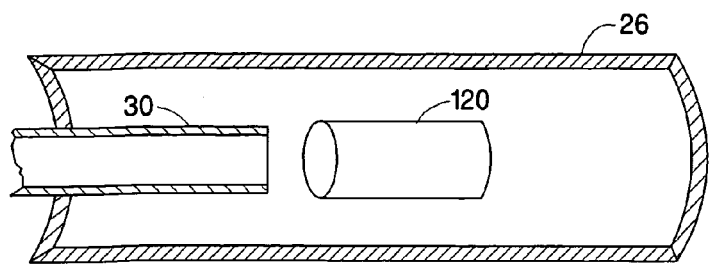
Figure 24C:
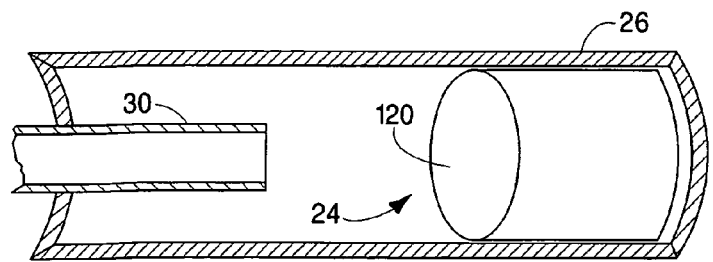

While the particles described herein can compose an embolic composition having a plurality of particles, in certain embodiments, an embolic composition includes only one particle. Referring to FIGS. 24A-24C, an embolic particle 120 (as shown, an elongated cylindrical particle) can be delivered to target site 24 in vessel 26 using catheter 30. During delivery, particle 120 is in a first state (e.g., a compacted state) as it passes through catheter 30. After particle 120 is released from catheter 30, the particle is transformed to a second state (e.g., an expanded state), and in the second state, the particle travels through vessel 26 and occludes the vessel. Subsequently, smaller particles (e.g., as described herein) can be introduced to fill or block any voids between particle 120 and vessel 26. Alternatively or in addition, smaller particles (e.g., as described herein) can be introduced before particle 120 is delivered to provide additional occlusion. Specific dimensions of particle 120 can be a function of the vessel in which the particle is to be used. In some embodiments, particle 120 has a final, average cross sectional diameter of about one millimeter to about forty-six millimeters. The length of particle 120 can be about one micron to about 50 mm, e.g., between about 3 and about 25 mm. Particle 120 can be formed into any of the shapes described herein using the material(s) described herein.

The embolic particles can be used to embolize vascular malformations and tumors, for example as a preoperative procedure to reduce surgical morbidity and/or mortality related to excessive interoperative blood loss. In these cases, occlusion of body vessels is typically temporary. In other cases, embolization is used as a definitive treatment, such as when the patient is not considered a good surgical candidate (e.g., because of poor heath, previously unsuccessful surgical attempts, inaccessible surgical site, traumatic hemorrhagic conditions, and/or high surgical risk). In these cases, occlusion of vessels is typically permanent. For example, embolization of internal mammary arteries and lumbar arteries can be used in endovascular abdominal aortic aneurysm repairs to treat Type 2 endoleaks.

Furthermore, in other embodiments, the embolic compositions can be used as pharmaceutically acceptable compositions in the treatment of, for example, fibroids, tumors, internal bleeding, AVMs, hypervascular tumors, fillers for aneurysm sacs, endoleak sealants, arterial sealants, puncture sealants and occlusion of other lumens such as fallopian tubes. Fibroids can include uterine fibroids which grow within the uterine wall (intramural type), on the outside of the uterus (subserosal type), inside the uterine cavity (submucosal type), between the layers of broad ligament supporting the uterus (interligamentous type), attached to another organ (parasitic type), or on a mushroom-like stalk (pedunculated type). Internal bleeding includes gastrointestinal, urinary, renal and varicose bleeding. AVMs are for example, abnormal collections of blood vessels, e.g. in the brain, which shunt blood from a high pressure artery to a low pressure vein, resulting in hypoxia and malnutrition of those regions from which the blood is diverted.

The magnitude of a therapeutic dose of the embolic composition can vary based on the nature, location and severity of the condition to be treated and the route of administration. A physician treating the condition, disease or disorder can determine effective amount of embolic composition. An effective amount of embolic composition refers to the amount sufficient to result in amelioration of symptoms or a prolongation of survival of the patient. The embolic compositions can be administered as pharmaceutically acceptable compositions to a patient in any therapeutically acceptable dosage, including those administered to a patient intravenously, subcutaneously, percutaneously, intratrachealy, intramuscularly, intramucosaly, intracutaneously, intra-articularly, orally or parenterally.

Compositions containing the embolic particles can be prepared in calibrated concentrations of the embolic particles for ease of delivery by the physician. The density of the composition can be from about 1.1 to 1.4 g/cm$^3$, or from about 1.2 to about 1.3 g/cm$^3$ in saline solution. Suspensions of the embolic particles in saline solution can be prepared to form stable suspensions over duration of time. The suspensions of embolic particles can be stable from 1 to 10 minutes, 2-7 minutes or 3 to 6 minutes. The physician can determine concentration of embolic particles by adjusting the weight ratio of the embolic particles to physiological solution. If weight ratio of the embolic particles is too small, too much liquid could be injected in a blood vessel, possibly allowing the embolic particles to stray into lateral vessels. In embodiments, the weight ratio of the embolic particles to the physiological solution is about 0.01 to 15% by weight.

In other embodiments, the embolic particles can be used for lung volume reduction, such as to treat any of the Chronic Obstructive Pulmonary Diseases (COPD). For example, a portion of the lung may be collapsed by obstructing an air passageway communicating with the portion of the lung to be collapsed. The air passageway may be obstructed by placing the embolic particles in the air passageway. The particles prevent air from being inhaled into or exhaled from the lung portion. Once the air passageway is sealed, the residual air within the lung can be absorbed over time to cause the lung portion to collapse. In other embodiments, the lung portion can be collapsed by inserting a conduit into the air passageway communicating with the lung portion, pulling a vacuum in the lung portion through the conduit to collapse the lung portion, and maintaining the lung portion in a collapsed state by sealing the air passageway with the embolic particles. To efficiently pull the vacuum in the lung portion to be collapsed, the space between the outer surface of the conduit and the inner surface of the air passageway may be sealed as the vacuum is pulled. The air passageway can be sealed while the lung portion is collapsed.

In some embodiments, the embolic particles described above can be used for tissue bulking. For example, the particles can be used to treat intrinsic sphincteric deficiency (ISD), vesicoureteral reflux, gastroesophageal reflux disease (GERD), and vocal cord paralysis, e.g., to restore glottic competence in cases of paralytic dysphonia. The particles can be used as a graft material or a filler to fill and/or to smooth out soft tissue defects, such as for reconstructive or cosmetic applications, e.g., surgery. Examples of applications include reconstruction of cleft lips; scars, e.g., depressed scars from chicken pox or acne scars; indentations resulting from liposuction; wrinkles, e.g., glabella frown wrinkles; and soft tissue augmentation of thin lips. Other applications are described in U.S. Ser. No. 10/231,664, filed Aug. 30, 2002, hereby incorporated by reference.

All publications, applications, references, and patents referred to in this application are herein incorporated by reference in their entirety.

Other embodiments are within the claims.

What is claimed is:

1. A composition, comprising:
   a first collection of embolic particles having a first shape; and
   a second collection of embolic particles having a second shape different than the first shape, wherein the first shape and the second shape are interlocking shapes.

2. The composition of claim 1, wherein the first shape is substantially free of a concave region.

3. The composition of claim 2, wherein the first shape is substantially spherical.

4. The composition of claim 1, wherein the second shape is flake-like.

5. The composition of claim 1, wherein the second shape is strand-like.

6. The composition of claim 1, wherein the second shape includes a generally convex region.

7. The composition of claim 1, wherein the second shape comprises a fibrous element extending from a base.

8. The composition of claim 1, wherein the particles in the first collection and the particles in the second collection have different compositions.

9. The composition of claim 1, wherein the particles of at least one of the collections comprise a radiopaque material.

10. The composition of claim 1, wherein the particles of at least one of the collections comprises a shape memory material and a non-shape memory material.

11. The composition of claim 1, wherein the particles of the first collection is spherical, and the particles of the second collection are non-spherical.

12. The composition of claim 1, wherein the particles of the first and second collections have different hardness.

13. The composition of claim 1, wherein the particles of at least one of the collections comprise a material capable of increasing in volume upon exposure to a predetermined stimulus.

14. The composition of claim 13, wherein the material comprises a hydrogel.

15. The composition of claim 1, wherein the particles in the first collection and the particles in the second collection have different sizes.

16. The composition of claim 15, wherein the size of the particles of at least one of the collections is about 1,200 microns or less.

17. The composition of claim 1, wherein the first and second collections are configured to engage with each other.

18. The composition of claim 1, wherein the first collection comprises particles comprising a shape memory material.

19. The composition of claim 1, wherein the particles of at least one of the collections comprise a portion capable of dissolving in a body.

20. The composition of claim 1, wherein the composition comprises at least a portion of the first collection of embolic particles separated from the second collection of embolic particles.

21. The composition of claim 1, wherein the embolic particles of the first collection of embolic particles have an aspect ratio greater than one.

* * * * *

UNITED STATES PATENT AND TRADEMARK OFFICE
CERTIFICATE OF CORRECTION

PATENT NO. : 7,588,825 B2
APPLICATION NO. : 10/700970
DATED : September 15, 2009
INVENTOR(S) : Bell et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1269 days.

Signed and Sealed this

Twenty-first Day of September, 2010

David J. Kappos
*Director of the United States Patent and Trademark Office*